(12) United States Patent
Kornman et al.

(10) Patent No.: US 10,337,070 B2
(45) Date of Patent: *Jul. 2, 2019

(54) METHODS AND KITS FOR TREATING CARDIOVASCULAR DISEASE

(71) Applicant: CARDIOFORECAST LTD., London (GB)

(72) Inventors: Kenneth S. Kornman, Newton, MA (US); Lynn Doucette-Stamm, Framingham, MA (US); Gordon W. Duff, Sheffield (GB)

(73) Assignee: CardioForecast Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,175

(22) Filed: Jul. 13, 2017

(65) Prior Publication Data

US 2018/0195121 A1 Jul. 12, 2018

Related U.S. Application Data

(60) Provisional application No. 62/445,395, filed on Jan. 12, 2017.

(51) Int. Cl.
 *C12Q 1/68* (2018.01)
 *C12Q 1/6883* (2018.01)
 *C12Q 1/6827* (2018.01)

(52) U.S. Cl.
 CPC ......... *C12Q 1/6883* (2013.01); *C12Q 1/6827* (2013.01); *C12Q 2600/156* (2013.01); *C12Q 2600/158* (2013.01); *G01N 2800/32* (2013.01)

(58) Field of Classification Search
 None
 See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,988,167 A | 1/1991 | Fergason |
| 4,988,617 A | 1/1991 | Landegren |
| 5,118,801 A | 6/1992 | Lizardi |
| 5,210,015 A | 5/1993 | Gelfand |
| 5,270,184 A | 12/1993 | Walker |
| 5,312,728 A | 5/1994 | Lizardi |
| 5,399,491 A | 3/1995 | Kacian |
| 5,422,252 A | 6/1995 | Walker |
| 5,494,810 A | 2/1996 | Barany |
| 5,498,531 A | 3/1996 | Jarrell |
| 5,527,675 A | 6/1996 | Coull |
| 5,538,848 A | 7/1996 | Livak |
| 5,539,082 A | 7/1996 | Nielsen |
| 5,623,049 A | 4/1997 | Lobberding |
| 5,686,246 A | 11/1997 | Kornman |
| 5,698,399 A | 12/1997 | Duff |
| 5,714,331 A | 2/1998 | Vaerlose |
| 5,808,918 A | 9/1998 | Fink |
| 5,830,711 A | 11/1998 | Barany |
| 5,866,336 A | 2/1999 | Nazarenko |
| 6,027,889 A | 2/2000 | Barany |
| 6,027,923 A | 2/2000 | Wallace |
| 6,054,564 A | 4/2000 | Barany |
| 6,108,635 A | 8/2000 | Herren |
| 6,117,635 A | 9/2000 | Nazarenko |
| 6,140,047 A | 10/2000 | Duff |
| 6,210,877 B1 | 4/2001 | Francis |
| 6,251,598 B1 | 6/2001 | Di Giovine |
| 6,268,142 B1 | 7/2001 | Duff |
| 6,268,148 B1 | 7/2001 | Barany |
| 6,383,775 B1 | 5/2002 | Duff |
| 6,437,216 B1 | 8/2002 | Duff |
| 6,524,795 B1 | 2/2003 | Francis |
| 6,551,785 B2 | 4/2003 | Di Giovine |
| 6,558,905 B1 | 5/2003 | Van Dijk |
| 6,706,478 B2 | 3/2004 | Duff |
| 6,713,253 B1 | 3/2004 | Duff |
| 6,720,141 B1 | 4/2004 | Crossman |
| 6,730,476 B1 | 5/2004 | Duff |
| 6,733,967 B1 | 5/2004 | Kornman |
| 6,746,839 B1 | 6/2004 | Duff |
| 7,723,028 B2 | 5/2010 | Kornman |
| 7,820,383 B2 | 10/2010 | Francis |
| 8,101,360 B2 | 1/2012 | Kornman |
| 8,105,775 B2 | 1/2012 | Kornman |
| 9,347,090 B2 | 5/2016 | Kornman et al. |
| 2002/0182612 A1 | 12/2002 | Duff |
| 2003/0100031 A1 | 5/2003 | Dower |
| 2003/0124524 A1 | 7/2003 | Kornman |
| 2003/0152947 A1 | 8/2003 | Crossman |
| 2003/0175764 A1 | 9/2003 | Francis |

(Continued)

FOREIGN PATENT DOCUMENTS

| | | |
|---|---|---|
| EP | 235726 | 9/1987 |
| WO | WO 89/11548 | 11/1989 |

(Continued)

OTHER PUBLICATIONS

Choudhury et al; Journal of the American College of Cardiology, vol. 68, pp. 1769-1780; Oct. 2016.*
Latella et al; Immunological Investigations; vol. 38, pp. 203-219, 2009.*
www.fda.gov/downloads/RegulatoryInformation/Guidances/ucm129296.pdf.
Araya et al., "Deep mutational scanning: assessing protein function on a massive scale", Trends in Biotechnology, vol. 29, No. 9, p. 435-442, (2011).
Boyle, J.P., et al., Projection of diabetes burden through 2050: impact of changing demography and disease prevalence in the U.S. Diabetes Care, 24(11), p. 1936-40, (2001).

(Continued)

*Primary Examiner* — Jehanne S Sitton
(74) *Attorney, Agent, or Firm* — Cooley LLP; Cynthia A. Kozakiewicz; Ivor R. Elrifi

(57) ABSTRACT

The present invention relates, in part, to methods and kits for treating cardiovascular disease.

2 Claims, 8 Drawing Sheets

(56) References Cited

U.S. PATENT DOCUMENTS

| | | |
|---|---|---|
| 2003/0235890 A1 | 12/2003 | Wyllie |
| 2004/0110168 A1 | 6/2004 | Van Dijk |
| 2004/0152124 A1 | 8/2004 | Duff |
| 2005/0032077 A1 | 2/2005 | Duff |
| 2005/0064453 A1 | 3/2005 | Duff |
| 2005/0171338 A1 | 8/2005 | Dower |
| 2005/0282198 A1 | 12/2005 | Duff |
| 2006/0183161 A1 | 8/2006 | Nicklin |
| 2006/0252050 A1 | 11/2006 | Ordovas |
| 2007/0264645 A1 | 11/2007 | Kornman |
| 2007/0275104 A1 | 11/2007 | Kornman |
| 2008/0118920 A1 | 5/2008 | Duff |
| 2008/0187920 A1 | 8/2008 | Duff |
| 2008/0199865 A1 | 8/2008 | Crossman |
| 2008/0254476 A1 | 10/2008 | Kornman |
| 2008/0254477 A1 | 10/2008 | Kornman |
| 2008/0254478 A1 | 10/2008 | Kornman |
| 2008/0311581 A1 | 12/2008 | Wyllie |
| 2009/0023147 A1 | 1/2009 | Kornman |
| 2009/0093396 A1 | 4/2009 | Crossman |
| 2009/0098141 A1 | 4/2009 | Kornman et al. |
| 2009/0163460 A1 | 6/2009 | Duff |
| 2009/0170105 A1 | 7/2009 | Kornman |
| 2009/0191564 A1 | 7/2009 | Francis |
| 2010/0028893 A1 | 2/2010 | Kornman |
| 2010/0098775 A1 | 4/2010 | Bukowski |
| 2010/0098809 A1 | 4/2010 | Bender |
| 2010/0105038 A1 | 4/2010 | Draper |
| 2010/0112570 A1 | 5/2010 | Aziz |
| 2010/0129798 A1 | 5/2010 | Abramson |
| 2010/0136561 A1 | 6/2010 | Draper |
| 2010/0255475 A1 | 10/2010 | Kornman |
| 2010/0279280 A1 | 11/2010 | Wyllie |
| 2011/0008906 A1 | 1/2011 | Aziz |
| 2012/0208187 A1 | 8/2012 | Kornman |
| 2013/0011841 A1 | 1/2013 | Aziz |
| 2013/0337448 A1 | 12/2013 | Kornman et al. |
| 2014/0356356 A1* | 12/2014 | Thuren ............ C07K 16/245 424/133.1 |
| 2017/0198350 A1 | 7/2017 | Doucette-Stamm |
| 2018/0195122 A1 | 7/2018 | Kornman et al. |

FOREIGN PATENT DOCUMENTS

| | | |
|---|---|---|
| WO | WO 93/22456 | 11/1993 |
| WO | WO 94/16101 | 7/1994 |
| WO | WO 97/31256 | 8/1997 |
| WO | WO 00/56927 | 9/2000 |
| WO | WO 2010/048378 A2 | 4/2010 |
| WO | WO 2012/079010 A2 | 6/2012 |
| WO | WO 2013/173789 A2 | 11/2013 |
| WO | WO 2014/179625 A1 | 11/2014 |
| WO | WO 2017/123696 A1 | 7/2017 |

OTHER PUBLICATIONS

Chen et al., "Single nucleotide polymorphism genotyping: biochemistry, protocol, cost and throughput," Pharmacogenomics J 3 (2):77-96 (2003).
Cohen et al., Advances in Chromatography 36:127-162 (1996).
Corey, "Peptide nucleic acids: expanding the scope of nucleic acid recognition," Trends Biotechnol 15 (6):224-9 (1997).
Flegal, K.M., et al., "Prevalence and trends in obesity among US adults, 1999-2000", JAMA, vol. 288, No. 14, p. 1723-1727.
Gibbs, R. A. et al. "Detection of single DNA base differences by competitive oligonucleotide priming", Nucleic Acid Res 17, p. 2427-2448 (1989).
Goodman & Gilman's The Pharmacological Basis of Therapeutics, Twelfth Edition (2011), Appendix II, pp. 1891-1991, and the Physicians' Desk Reference 70$^{th}$ Edition, 2016.
Griffin et al. "DNA Sequencing, Recent Innovations and Future Trends", Appl Biochem Biotechnol 38:147-159 (1993).
Guatelli et al., "Isothermal, in vitro amplification of nucleic acids by a multienzyme reaction modeled after retroviral replication", Proc Natl Acad Sci USA 87:1874 (1990).
Hyrup et al., "Peptide nucleic acids (PNA): synthesis, properties and potential applications," Bioorganic & Medicinal Chemistry 4 (1):5-23 (1996).
Ingkanisorn et al., "Prognosis of Negative Adenosine Stress Magnetic Resonance in Patients Presenting to an Emergency Department With Chest Pain", J. Am. Coll. Cardiol. 47(7): 1427-1432 (2006).
Kwok et al., "Detection of single nucleotide polymorphisms," Curr Issues Mol Biol 5 (2):43-60 (2003).
Kwok, "Methods for genotyping single nucleotide polymorphisms," Annu Rev Genom Hum Genet 2:235-58 (2001).
Lancet, "Estimation of contribution of changes in coronary care to improving survival, event rates, and coronary heart disease mortality across the WHO MONICA Project populations", 355(9205), p. 688-700 (2000).
Landegren et al., "A Ligase-Mediated Gene Detection Technique", Science 241:1077 (1988).
Li et al., "The sequence and de novo assembly of the giant panda genome", Nature 463: 311-317 (2010).
Libby "Current concepts of the pathogenesis of the acute coronary syndromes" Circulation 140:365-372 (2001).
Libby, P., "History of Discovery: Inflammation in Atherosclerosis." Arterioscler Thromb Vasc Biol. 32(9): 2045-2015, (2012).
Livak et al., "Oligonucleotides with Fluorescent Dyes at Opposite Ends Provide a Quenched Probe System Useful for Detecting PCR Product and Nucleic Acid Hybridization", PCR Method Appl 4:357-362 (1995).
Lo et al., "Next-Generation Sequencing of Plasma/Serum DNA: An Emerging Research and Molecular Diagnostic Tool", Clin Chem 55: 607-608 (2009).
Marcucci et al., "Cardiovascular Death and Nonfatal Myocardial Infarction in Acute Coronary Syndrome Patients Receiving Coronary Stenting Are Predicted by Residual Platelet Reactivity to ADP Detected by a Point-of-Care Assay", Circulation 119:237-242, (2009).
Marnellos, "High-throughput SNP analysis for genetic association studies," Curr Opin Drug Disc Devel 6 (3):317-21 (May 2003).
Martin-Ventura et al., "Biomarkers in Cardiovascular Medicine", Rev. Esp. Cardiol 62(6), 677-688 (2009).
McEllistrem, "Genetic diversity of the pneumococcal capsule: implications for molecular-based serotyping", Future Microbiol 4: 857-865 (2009).
Murray and Lopez, "Mortality by cause for eight regions of the world: Global Burden of Disease Study", Lancet 349:1269-1276, 1997.
Myers et al., "Detection of single base substitutions in total genomic DNA", Nature 313:495 (1985).
Nazarenko et al., "A closed tube format for amplification and detection of DNA based on energy transfer", Nucleic Acids Res 25:2516-2521 (1997).
Pelak et al., "The Characterization of Twenty Sequenced Human Genomes", PLoS Genetics 6:9, p. e1001111 (2010).
Ram et al., "Getting to Know Our Guests: Characterizing the Reproductive Microbiome by Next Generation Sequencing", Syst Biol Reprod Med 57(3):117-118 (2011).
Rasmussen et al., "Ancient human genome sequence of an extinct Palaeo-Eskimo", Nature 463:757-762 (2010).
Ray, KK., "Interleukin-1 Revisited: Further Insights Into Its Role in Atherosclerosis and as a Potential Therapeutic Target for Treatment." *Journal of the American College of Cardiology* (2014), 63.17: 1735-1738.
Ridker PM et al. "Rosuvastatin to prevent vascular events in men and women with elevated C-reactive protein", N Engl J Med., 359, p. 2195-2207, 2008.
Ridker, P. M. "Targeting inflammatory pathways for the treatment of cardiovascular disease." *European Heart Journal* 35 (2014).
Robinson, "Whole-exome sequencing for finding de novo mutations in sporadic mental retardation", Genome Biol 11:144 (2010).
Rogus J., et al., "IL1B Gene Promoter Haplotype Pairs Predict Clinical Levels of Interleukin-1β and C-reactive Protein." *Human Genetics* 123.4: 387-398, (2008).

(56) References Cited

OTHER PUBLICATIONS

Ross "Atherosclerosis—An inflammatory disease" N Engl J Med 340:115-126, (1999).
Saiki et al., "Analysis of enzymatically amplified β-globin and HLA-DQα DNA with allele-specific oligonucleotide probes", Nature 324:163-166 (1986).
Schillinger et al., "Acute chest pain—identification of patients at low risk for coronary events. The impact of symptoms, medical history and risk factors", Wiener Klin. Wochenschr. 116(3): 83-89, (2004).
Selvaraj et al., "Point-of-Care Determination of Baseline Platelet Function as a Predictor of Clinical Outcomes in Patients who Present to the Emergency Department with Chest Pain", J. Throm. Thrombolysis 18(2): 109-115, 2004.
Sharma et al., "Coronary computed tomographic angiography (CCTA) in community hospitals: 'current and emerging role'", Vasc. Health Risk Manag. 6:307-316, 2010.
Sharma et al., supra; Cury et al., "Acute chest pain imaging in the emergency department with cardiac computed tomography angiography", J. Nucl. Cardiol. 15 (4): 564-575, 2008.
Shi, "Technologies for individual genotyping: detection of genetic polymorphisms in drug targets and disease genes," Am J Pharmacogenomics 2 (3):197-205 (2002).
Srivatsan et al., "High-Precision, Whole-Genome Sequencing of Laboratory Strains Facilitates Genetic Studies", PLoS Genet 4: e100139 (2008).
Tadros et al., "Clinical Predictors of 30-day Cardiac Events in Patients with Acute Coronary Syndrome at a Community Hospital", South Med. J. 96, p. 1113-1120, 2003.
Tsimikas S. et al., "Antisense oligonucleotides targeting apolipoprotein(a) in people with raised lipoprotein(a): two randomized, double-blind, placebo controlled, dose-ranging trials" The Lancet, (2016).
Tsimikas S. et al., "Oxidized Phospholipids, Lp(a) Lipoprotein, and Coronary Artery Disease." New England Journal of Medicine 353:46-57, (2005).
Tsmikas S. et al., "Pro-Inflammatory Interleukin-1 Genotypes Potentiate the risk of Coronary Artery Disease and Cardiovascular Events Mediated by Oxidized Phospholipids and Lipoprotein(a)" J. Am. College of Cardiology vol. 63, No. 17, (2014).
Tyagi et al., "Molecular Beacons: Probes that Fluoresce upon Hybridization", Nature Biotechnology 14:303-308 (1996).
Wise et al., "A standard protocol for single nucleotide primer extension in the human genome using matrix-assisted laser desorption/ionization time-of-flight mass spectrometry," Rapid Comm. Mass Spect. 17 (11):1195-202 (2003).
Wong, M.D., et al., "Contribution of major diseases to disparities in mortality", N Engl J Med, 347(20), p. 1585-92, (2002).
Wu and Wallace, "The Ligation Amplification Reaction (LAR)-Amplification of Specific DNA Sequences Using Sequential Rounds of Template-Dependent Ligation", Genomics 4:560 (1989).
Yusuf, S., et al., "Global burden of cardiovascular diseases: Part II: variations in cardiovascular disease by specific ethnic groups and geographic regions and prevention strategies", Circulation, 104(23): p. 2855-64, 2001.
Yusuf, S., et al "Global burden of cardiovascular diseases: part I: general considerations, the epidemiologic transition, risk factors, and impact of urbanization", Circulation, 104(22), p. 2746-53, 2001.
Yusuf et al., "Effect of potentially modifiable risk factors associated with myocardial infarction in 52 countries (the INTERHEART study): case-control study" Lancet, 364:937-52 (2004).
<https://clinicaltrials.gov/ct2/show/study/NCT02160899>, Clinical Trials, Identifier NCT02160899, U.S. National Library of Medicine, Jun. 11, 2014, 18 pages.
Bailly, S. et al., "Genetic polymorphism of human interleukin-1 alpha," Eur J Immunol 23:1240-1245 (1993).
Bailly, S. et al., "Polymorphic tandem repeat region in interleukin-1 alpha intron 6," Hum Genet 91:85-86 (1993).
Bailly, S. et al., "An intronic polymorphic repeat sequence modulates interleukin-1 alpha gene regulation," Mol Immunol 33:999-1006 (1996).
Berger, P. et al., "C-reactive protein levels are influenced by common IL-1 gene variations," Cytokine 17:171-174 (2002).
Bioque, G. et al., "Allelic polymorphism in IL-1β and IL-1 receptor antagonist (IL-1Ra) genes in inflammatory bowel disease," Clin Exp Immunol 102:379-383 (1995).
Blakemore, A. I. et al., "Interleukin-1 receptor antagonist gene polymorphism as a disease severity factor in systemic lupus erythematosus," Arthritis Rheum 37:1380-1385 (1994).
Blakemore, A. I. et al., "Interleukin-1 receptor antagonist allele (IL1RN*2) associated with nephropathy in diabetes mellitus," Hum Genet 97:369-374 (1996).
Camp, N. J. et al., "Evidence of a pharmacogenomic response to interleukin-I receptor antagonist in rheumatoid arthritis," Genes Immun 6:467-471 (2005).
Carter, M. J. et al., "Functional correlates of the interleukin-1 receptor antagonist gene polymorphism in the colonic mucosa in ulcerative colitis," Genes Immun 5:8-15 (2004).
Carter, K. W. et al., "Association of Interleukin-1 gene polymorphisms with central obesity and metabolic syndrome in a coronary heart disease population," Hum Genet, vol. 124, No. 3, pp. 199-206 (2008).
Chen, H. et al., "Single nucleotide polymorphisms in the human interleukin-1B gene affect transcription according to haplotype context," Hum Mol Genet 15:519-529 (2006).
Chen, X. et al., "Association of six CpG-SNPs in the inflammation-related genes with coronary heart disease," Human Genomics, 2016, vol. 10, No. S2, doi: 10.1186/s40246-016-0067-1, 7 pages.
Clay, F. E. et al., "Interleukin 1 receptor antagonist gene polymorphism association with lichen sclerosis," Hum Genet 94:407-410 (1994).
Clay, F. E. et al., "Novel interleukin-1 receptor antagonist exon polymorphisms and their use in allele-specific mRNA assessment," Hum Genet 97:723-726 (1996).
Cominelli, F. & Pizarro, T. T., "Interleukin-1 and interleukin-1 receptor antagonist in inflammatory bowel disease," Aliment Pharmacol Ther 10, Suppl 2:49-53; discussion 54 (1996).
Cork, M. J. et al., "Psoriasis and interleukin-1. A translation," J R Coll Physicians Lond 27:366 (1993).
Dennis, R. A. et al., "Interleukin-1 polymorphisms are associated with the inflammatory response in human muscle to acute resistance exercise," J Physiol 560:617-626 (2004).
Di Giovine, F. S. et al., "Single base polymorphism at—511 in the human interleukin-1 beta gene (IL1 beta)," Hum Mol Genet 1:450 (1992).
Duff, G. W., "Genetic variation in cytokines and relevance to inflammation and disease," In: Balkwill F, ed. The Cytokine Network Frontiers in Molecular Biology, vol. 25. Oxford: Oxford University Press, 2000:152-173.
Francis, S. E. et al., "Interleukin-1 receptor antagonist gene polymorphism and coronary artery disease," Circulation 99:861-866 (1999).
Genevay, S. et al., "Association of interleukin-4 and interleukin-1B gene variants with Larsen score progression in rheumatoid arthritis," Arthritis Rheum 47:303-309 (2002).
Giannobile, W. V. et al., "Patient Stratification for Preventive Care in Dentistry," Journal of Dental Research 92(8):694-701 (2013).
Grutters, J. C. et al., "Analysis of IL6 and IL1A gene polymorphisms in UK and Dutch patients with sarcoidosis," Sarcoidosis Vasc Diffuse Lung Dis 20:20-27 (2003).
Harrison, P. et al., "Interleukin-1 promoter region polymorphism role in rheumatoid arthritis: a meta-analysis of IL-1B-511A/G variant reveals association with rheumatoid arthritis," Rheumatology 47(12):1768-1770 (2008).
Heresbach, D. et al., "Significance of interleukin-1beta and interleukin-1 receptor antagonist genetic polymorphism in inflammatory bowel diseases," Am J Gastroenterol 92:1164-1169 (1997).
Hutyrova, B. et al., "Interleukin-1 gene cluster polymorphisms in sarcoidosis and idiopathic pulmonary fibrosis," Am J Respir Crit Care Med 165:148-151 (2002).

(56) References Cited

OTHER PUBLICATIONS

Guidance for Industry, E15 Definitions for Genomic Biomarkers, Pharmacogenomics, Pharmacogenetics, Genomic Data and Sample Coding Categories, Food & Drug Administration, Apr. 2008, 10 pages; fda.gov/Drugs/DevelopmentApprovalProcess/FromsSubmissionRequirement/ElectronicSubmissions/DataStandardsManualmonographs/ucm071667.htm.

Iacoviello, L. et al., "Polymorphisms of the interleukin-1beta gene affect the risk of myocardial infarction and ischemic stroke at young age and the response of mononuclear cells to stimulation in vitro," Arterioscler Thromb Vasc Biol 25:222-227 (2005).

Joo, C.-K. et al., "A Genetic Association of Proinflammatory Cytokine Genes in Korean Dry Eye Patients," ARVO Annual Meeting Abstract Search and Program Planner, vol. 52, May 2011, & Annual Meeting of the Association for Research in Vision and Ophthalmology (ARVO), 2 pages.

Jouvenne, P. et al., "Possible genetic association between interleukin-1alpha gene polymorphism and the severity of chronic polyarthritis," Eur Cytokine Netw 10:33-36 (1999).

Kapelski, P. et al., "Association study of functional polymorphisms in interleukins and interleukin receptors genes: IL1A, IL1B, IL1RN, IL6, IL6R, IL10, IL10RA and TGFB1 in schizophrenia in Polish population," Schizophrenia Research, vol. 169, No. 1-3, pp. 1-9 (2015).

Kastrati, A. et al., "Protective role against restenosis from an interleukin-1 receptor antagonist gene polymorphism in patients treated with coronary stenting," J Am Coll Cardiol 36:2168-2173 (2000).

Kornman, K. S. et al., "The interleukin-1 genotype as a severity factor in adult periodontal disease," Journal of clinical periodontology 24:72-77 (1997).

Lavigne, P. M. & Karas, R. H. et al., "The Current State of Niacin in Cardiovascular Disease Prevention," Journal of the American College of Cardiology, vol. 61, pp. 440-446 (2013).

Mansfield, J. et al., "Novel genetic association between ulcerative colitis and the anti-inflammatory cytokine interleukin-1 receptor antagonist," Gastroenterology 106:637-642 (1994).

McDowell, T. L. et al., "A genetic association between juvenile rheumatoid arthritis and a novel interleukin-1 alpha polymorphism," Arthritis Rheum 38:221-228 (1995).

Na, K.-S. et al., "Proinflammatory gene polymorphisms are potentially associated with Korean non-Sjogren dry eye patients," Molecular Vision 17:2818-2823 (2011).

Nasibullin, T. R. et al., "Combinations of cytokine gene network polymorphic markers as potential predictors of myocardial infarction," Russian Journal of Genetics, vol. 50, No. 9, pp. 987-993 (2014).

Nemetez, A. et al., "IL1B gene polymorphisms influence the course and severity of inflammatory bowel disease," Immunogenetics 49:527-531 (1999).

Nicklin, M. J. H. et al., "A Sequence-Based Map of the Nine Genes of the Human Interleukin-1 Cluster," Genomics 79:718-725 (2002).

Ray, K. K. et al., "Genetic variation at the interleukin-1 locus is a determinant of changes in soluble endothelial factors in patients with acute coronary syndromes," Clinical Science 103:303-310 (2002).

Read, R. C. et al., "An interleukin-1 genotype is associated with fatal outcome of meningococcal disease," J Infect Dis 182:1557-1560 (2000).

Riha, R. L. et al., "Cytokine gene polymorphisms in idiopathic pulmonary fibrosis," Intern Med J 34:126-129 (2004).

Ruperto, N. et al., "Two randomized trials of canakinumab in systemic juvenile idiopathic arthritis," The New England Journal of Medicine 367:2396-2406 (2012).

Tarlow, J. K. et al., "Severity of alopecia areata is associated with a polymorphism in the interleukin-1 receptor antagonist gene," J Invest Dermatol 103:387-390 (1994).

Tarlow, J. K. et al., "Association between interleukin-1 receptor antagonist (IL-1ra) gene polymorphism and early and late-onset psoriasis," Br J Dermatol 136:147-148 (1997).

Thompson, P. L. & Nidorf, M. S., "Anti-inflammatory therapy with canakinumab for atherosclerotic disease: lessons from the CANTOS trial," Journal of Thoracic Disease 10(2):695-698 (2018).

Timms, A. E. et al., "The interleukin 1 gene cluster contains a major susceptibility locus for ankylosing spondylitis," American Journal of Human Genetics 75:587-595 (2004).

Tountas, N. A. et al., "Functional and ethnic association of allele 2 of the interleukin-1 receptor antagonist gene in ulcerative colitis," Gastroenterology 117:806-813 (1999).

Tsimikas, S. et al., "The Influence of Oxidized Phospholipids and Lp(a) Lipoprotein on Coronary Artery Disease is Conditional upon Genotype at the Interleukin-1 Region," American College of Cardiology Annual Meeting, New Orleans 2007, 1 page.

Vargas-Alarcón, G. et al., "The interleukin-1β-511 T>C (r516944) gene polymorphism is associated with risk of developing silent myocardial ischemia in diabetic patients," Immunology Letters, vol. 168, No. 1, pp. 7-12 (2015).

Whyte, M. et al., "Increased risk of fibrosing alveolitis associated with interleukin-1 receptor antagonist and tumor necrosis factor-alpha gene polymorphisms," Am J Respir Crit Care Med 162:755-758 (2000).

Yang, H. T. et al., "Association of interleukin gene polymorphisms with the risk of coronary artery disease," Genetics and Molecular Research, vol. 14, No. 4, pp. 12489-12496 (2015).

Yucesoy, B. et al., "Polymorphisms of the IL-1 gene complex in coal miners with silicosis," Am J Ind Med 39:286-291 (2001).

Zhang, G. et al., "A negative regulatory region containing a glucocorticosteroid response element (nGRE) in the human interleukin-1β gene," DNA Cell Biol 16:145-152 (1997).

U.S. Appl. No. 60/427,818, filed Nov. 19, 2002.
U.S. Appl. No. 60/445,494, filed Feb. 7, 2003.
U.S. Appl. No. 60/445,636, filed Feb. 7, 2003.

\* cited by examiner

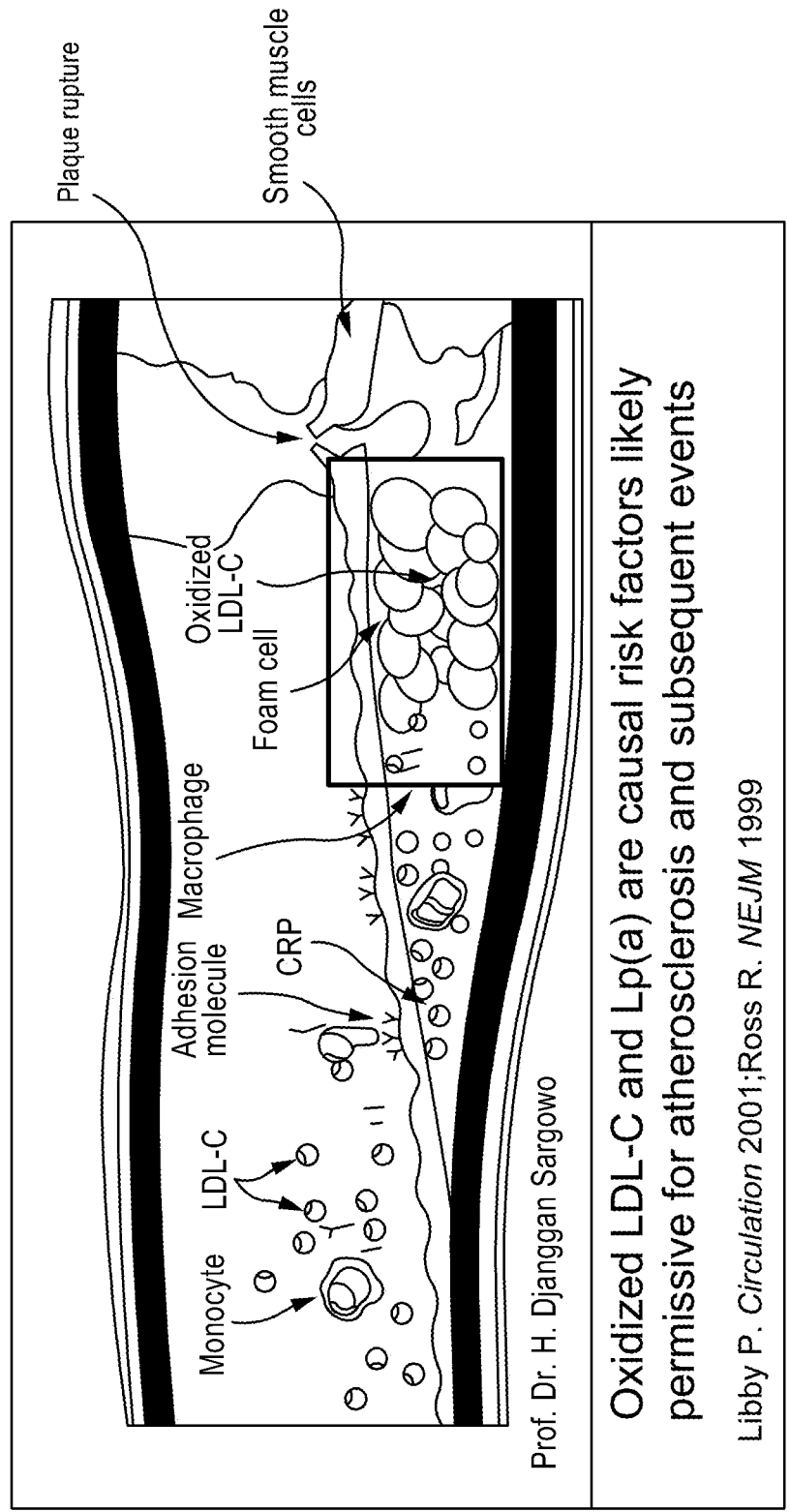

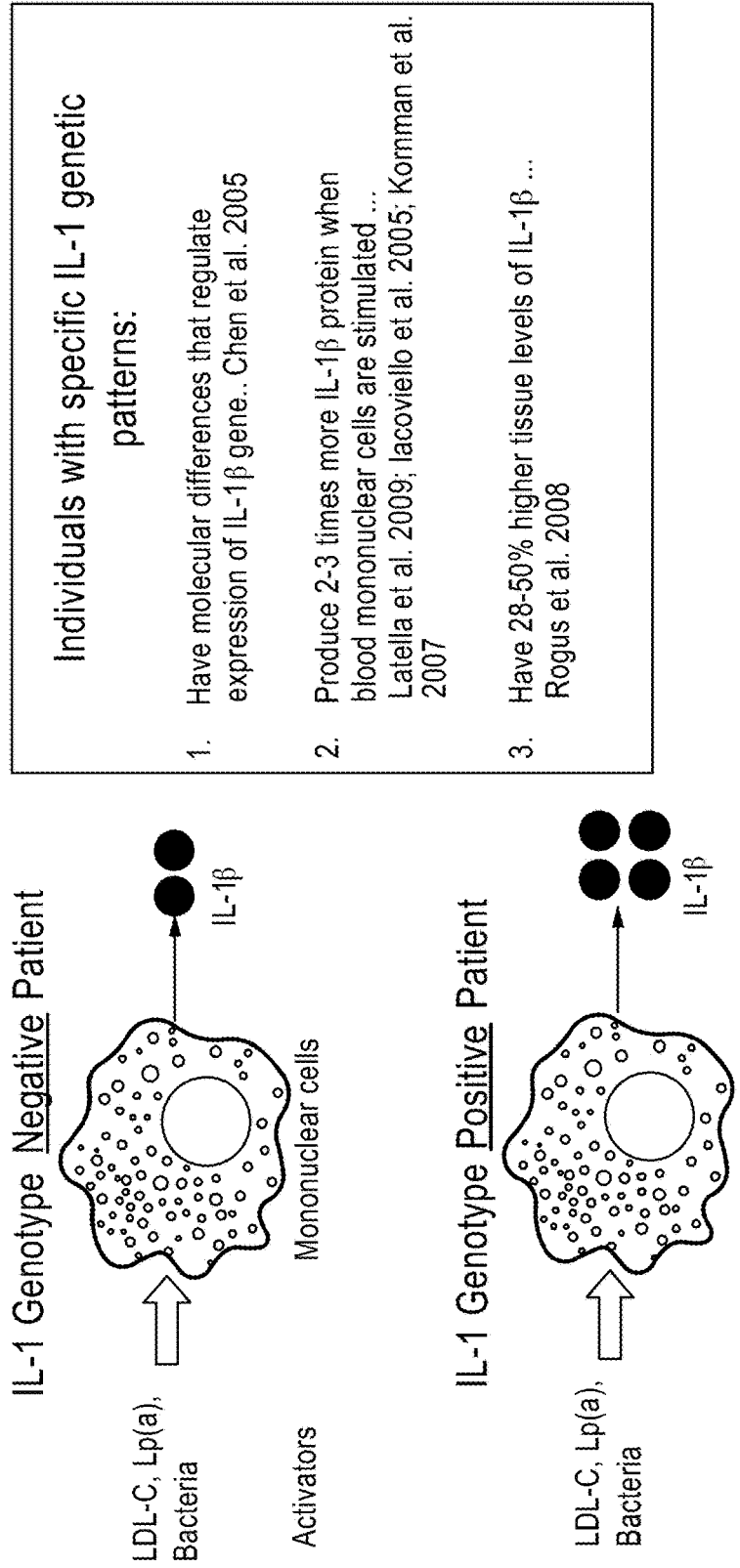

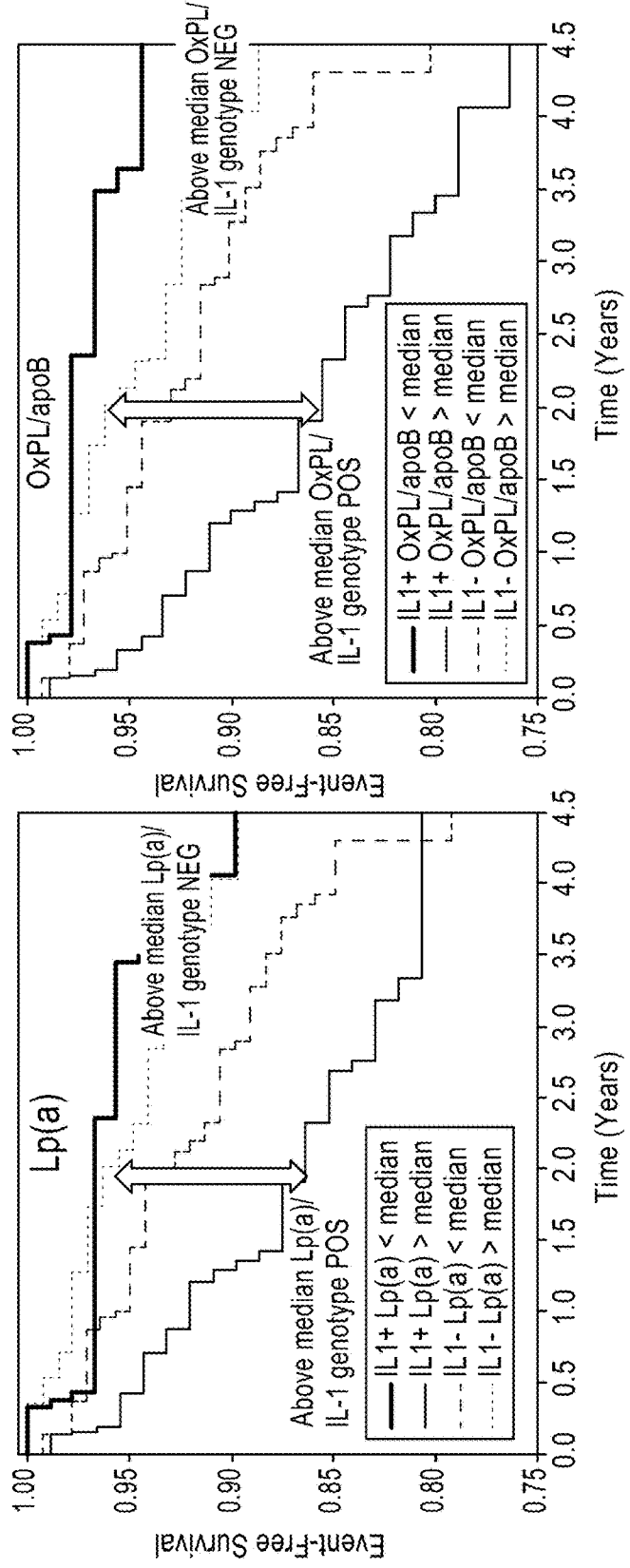

METHODS AND KITS FOR TREATING CARDIOVASCULAR DISEASE

RELATED APPLICATIONS

This application claims priority to and benefit of U.S. Provisional Application No. 62/445,395, filed on Jan. 12, 2017 the contents of which are incorporated herein in its entirety.

BACKGROUND OF THE INVENTION

Cardiovascular disease (CVD) is the leading cause of death globally. Each year in the U.S. there are 550,000 newly diagnosed CVD and there are 200,000 recurrent CVD events each year.

Currently, a primary method for treating or preventing CVD is use of statins to lower levels of cholesterol, more specifically low-density lipoprotein cholesterol (LDL-C). However, in 20% to 30% of CVD patients, statins are ineffective in preventing recurrent CV events. In a Mayo Clinic study and an unpublished recent European study, CVD patients treated with statins had a 6 to 20% second event rate within two years, even though these subjects experienced lowered LDL-C cholesterol levels following treatment with statins.

In the "Jupiter study" (Ridker P M, Danielson E, Fonseca F A H, Genest J, Gottto A M, Kastelein J J P, Koenig W, Libby P, Lorenzatti A J, MacFadyen J G, Nordestgaard B G, Shepherd J, Willerson J T, Glynn R J for the JUPITER Study Group. Rosuvastatin to prevent vascular events in men and women with elevated C-reactive protein. N Engl J Med. 2008; 359:2195-2207), subjects with elevated C-reactive protein (CRP) yet with low cholesterol levels were treated with high doses of the statin Crestor to determine whether the treatment reduced CRP and reduced first CVD events.

However, there exist subsets of CVD patients who respond (e.g., by lowering LDL-C cholesterol levels) to standard pharmacological treatments, yet remain susceptible to first or second recurrent CVD events. For example, in the JUPITER Study, of subjects treated with potent statin therapy, Lp(a) was a significant determinant of remaining risk for a first CVD event in spite of reduced LDL-C.

Accordingly, an unmet need exists for methods and kits to identify whether an individual who may be susceptible to recurrent CVD events—even with a standard pharmacological treatment—so that s/he can receive increased monitoring and/or be provided a more aggressive and optimal therapeutic intervention.

SUMMARY OF THE INVENTION

The present invention is based upon the discovery that specific IL-1 genotype patterns stratify individuals into groups relating to their member's likelihood of over-producing IL-1 and having an auto-inflammatory response in the vascular wall in response to one or more clinical indicators, including but not limited to Lp(a) levels, OxPL levels, triglyceride-rich lipoprotein levels, LDL-C levels, CRP levels, and hypertension.

The present invention, comprising an IL-1 genetic test in combination with Lp(a), for example, predicts approximately 60% of recurrent cardiac events and first events in individuals with Lp(a) and IL-1 genotype patterns that are pro-inflammatory. The present invention enables cardiologists to increase monitoring of and/or provide more aggressive, optimal treatments or preventative regimens to specific subsets of patients.

The invention provides a method of selecting a human subject with a diagnosis of, suspected of having, or at risk for cardiovascular disease; obtaining an isolated nucleic acid from a biological sample from the human subject; detecting the single nucleotide polymorphism (SNP) alleles in the isolated nucleic acid for each of the rs16944 polymorphic locus, the rs1143623 polymorphic locus, the rs4848306 polymorphic locus, the rs17561 polymorphic locus, and the rs1143634 polymorphic locus; determining the human subject's IL-1 pattern based on the detecting in step and the information disclosed in Table 1 and Table 2; measuring the status of one or more clinical indicators in the biological sample from the human subject, in another biological sample from the human subject, or in the human subject him/herself; and providing a recommendation for a therapeutic or preventative regimen based upon the human subject's IL-1 genotype pattern and measured status of one or more clinical indicators.

In various aspects the invention provides methods for predicting the risk of and preventing a future cardiac event in a human subject by obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus; determining whether the subject has a positive or negative IL-1 genotype pattern based on the information obtained and the information in Table 1 and Table 2; determining the plasma concentration of LDL-C and/or Lp(a) in a plasma sample obtained from the subject; predicting the subject is at risk of a future cardiac event when the subject has a positive IL-1 pattern and a total LDL-C plasma concentration of 70 mg/dL or less and/or a total Lp(a) plasma concentration of at least 5 mg/dL; and administering an IL-beta inhibitor to the subject. The IL-beta inhibitor is for example canakinumab. Optionally, the method further includes administering one or more drugs from Table 4.

In another aspect, the invention provides methods for determining whether a human subject would receive a therapeutic benefit from/would be responsive to IL-1 blocking drug and treating the subject by obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus; determining whether the subject has a positive or negative IL-1 genotype pattern based on the information and the information in Table 1 and Table 2; determining the plasma concentration of LDL-C and/or Lp(a) in a plasma sample obtained from the subject determining the subject would receive a therapeutic benefit from/would be responsive to a IL-1 blocking drug when the subject has a positive IL-1 pattern and a total LDL-C plasma concentration of 70 mg/dL or less and/or a total Lp(a) plasma concentration of at least 5 mg/dL; and administering an IL-1 blocking drug to the subject. The IL-1 blocking drug is for example canakinumab. Optionally, the method further includes administering one or more drugs from Table 4.

For example, when a human subject has a positive IL-1 pattern based on the information disclosed in Table 1 and Table 2 and has a measured status of the one or more clinical indicators above a threshold level for the one or more clinical indicator, the human subject is administered a treatment comprising at least one drug selected from Table 3 to Table 7 or is administered a treatment comprising at least one drug selected from Table 3 and at least one drug selected from Table 4 to Table 7.

Alternatively, when the human subject has a positive IL-1 pattern based on the information disclosed in Table 1 and Table 2 and has a measured status of the one or more clinical indicators below a threshold level for the one or more clinical indicator, the human subject is administered a treatment comprising at least one drug selected from Table 3 and not comprising at least one drug selected from Table 4 to Table 7 or is administered a treatment not comprising at least one drug selected from Table 4 to Table 7.

When the clinical indicator is Lp(a) and the human subject has levels of Lp(a) above a threshold value, the at least one drug is selected from Table 4 or the at least one drug is selected from Table 4 and further includes at least one drug selected from Table 5. Alternatively, when the clinical indicator is LDL-C and the human subject has levels of LDL-C above a threshold value, the at least one drug is selected from Table 5 or the at least one drug is selected from Table 5 and further includes at least one drug selected from Table 3. Additionally, when the clinical indicator is Triglyceride-rich lipoproteins and the human subject has levels of Triglyceride-rich lipoproteins above a threshold value, the at least one drug is selected from Table 6 or the at least one drug is selected from Table 6 and further includes at least one drug selected from Table 3. When the clinical indicator is blood pressure and the human subject has a blood pressure above a threshold value, the at least one drug is selected from Table 7 or the at least one drug is selected from Table 7 and further includes at least one drug selected from Table 3.

In another aspect the invention provides methods for treating a human subject having or at risk for cardiovascular disease by (a) obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus; (b) determining each human subject's IL-1 genotype pattern based on the information obtained in step (a) and the information disclosed in Table 1 and Table 2; (c) obtaining information regarding the human subject's status for one or more clinical indicators; and (d) administering a treatment comprising at least one drug selected from Table 4 to Table 7 or administering a treatment comprising at least one drug selected from Table 3 and at least one drug selected from Table 4 to Table 7 when the human subject has a positive IL-1 pattern based on the information disclosed in Table 1 and Table 2 and has a measured status of the one or more clinical indicators above a threshold level for the one or more clinical indicator, or administering a treatment comprising at least one drug selected from Table 3 and not comprising at least one drug selected from Table 4 to Table 7 or administering a treatment not comprising at least one drug selected from Table 4 to Table 7 when the human subject has a positive IL-1 pattern based on the information disclosed in Table 1 and Table 2 and has a measured status of the one or more clinical indicators below a threshold level for the one or more clinical indicator. When the clinical indicator is Lp(a) and the human subject has levels of Lp(a) above a threshold value, the at least one drug is selected from Table 4 or the at least one drug is selected from Table 4 and further includes at least one drug selected from Table 3. Alternatively, when the clinical indicator is LDL-C and the human subject has levels of LDL-C above a threshold value, the at least one drug is selected from Table 5 or the at least one drug is selected from Table 5 and further includes at least one drug selected from Table 3. When the clinical indicator is Triglyceride-rich lipoproteins and the human subject has levels of Triglyceride-rich lipoproteins above a threshold value, the at least one drug is selected from Table 6 or the at least one drug is selected from Table 6 and further includes at least one drug selected from Table 3. Alternatively, when the clinical indicator is blood pressure and the human subject has a blood pressure above a threshold value, the at least one drug is selected from Table 7 or the at least one drug is selected from Table 7 and further includes at least one drug selected from Table 3.

Also included in the invention are methods for determining whether a human subject is predisposed to having cardiovascular disease by (a) obtaining an isolated nucleic acid from a biological sample from the human subject; (b) detecting the single nucleotide polymorphism (SNP) alleles in the isolated nucleic acid for each of the rs16944 polymorphic locus, the rs1143623 polymorphic locus, the rs4848306 polymorphic locus, the rs17561 polymorphic locus, and the rs1143634 polymorphic locus; (c) determining the human subject's IL-1 pattern based on the detecting in step (b) and the information disclosed in Table 1 and Table 2; and (d) measuring the status of one or more clinical indicators in the biological sample from the human subject, in another biological sample from the human subject, or in the human subject him/herself. When the human subject has a positive IL-1 genotype pattern and has a measured status of the one or more clinical indicators above a threshold level for the one or more clinical indicator, the subject is predisposed to having cardiovascular disease.

In another aspect the invention provides methods for determining whether a human subject having cardiovascular disease would receive a therapeutic benefit from/would be responsive to a drug selected from Table 3 to Table 8, by (a) obtaining an isolated nucleic acid from a biological sample from the human subject; (b) detecting the single nucleotide polymorphism (SNP) alleles in the isolated nucleic acid for each of the rs16944 polymorphic locus, the rs1143623 polymorphic locus, the rs4848306 polymorphic locus, the rs17561 polymorphic locus, and the rs1143634 polymorphic locus; (c) determining the human subject's IL-1 pattern based on the detecting in step (c) and the information disclosed in Table 1 and Table 2; and (d) measuring the status of one or more clinical indicators in the biological sample from the human subject, in another biological sample from the human subject, or in the human subject him/herself. When the human subject has a positive IL-1 genotype pattern and has a measured status of the one or more clinical indicators above a threshold level for the one or more clinical indicator, the subject would receive a therapeutic benefit from/would be responsive to a drug selected from Table 4 to Table 7. Alternatively, when the human subject has a positive IL-1 genotype pattern and has a measured status of the one or more clinical indicators below a threshold level for the one or more clinical indicator, the subject would not receive a therapeutic benefit from/would not be responsive to a drug selected from Table 4 to Table 7. In various aspects the method further includes obtaining an isolated nucleic acid from a biological sample from the human subject; and detecting the single nucleotide polymorphism (SNP) alleles from the isolated nucleic acid for each of the rs16944 polymorphic locus, the rs1143623 polymorphic locus, the rs4848306 polymorphic locus, the rs17561 polymorphic locus, and the rs1143634 polymorphic locus and/or measuring the status of one or more clinical indicators in the biological sample from the human subject, in another biological sample from the human subject, or in the human subject him/herself.

In yet another aspect the invention provides a kit including reagents for detecting the single nucleotide polymorphism (SNP) alleles in an isolated nucleic acid for each of the rs16944 polymorphic locus, the rs1143623 polymorphic locus, the rs4848306 polymorphic locus, the rs17561 polymorphic locus, and the rs1143634 polymorphic locus; optionally, reagents for measuring the status of one or more clinical indicators; instructions for determining a human subject's IL-1 genotype pattern based on the detecting in step (a), and the information disclosed in Table 1 and Table 2; and instructions for determining whether a subject would receive a therapeutic benefit from/would be responsive to at least one drug selected from Table 3 to Table 7 or at least one drug selected from Table 3 and at least one drug selected from Table 4 to Table 7.

As used herein, one or more clinical indicators include for example, Lp(a), Triglyceride-rich lipoproteins, OxPL, LDL-C, CRP, or hypertension.

Also contemplated by the invention are the use of drugs having a mode of action similar to or identical to a drug selected from Table 3 to Table 7.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the following detailed description and claim.

BRIEF DESCRIPTION OF THE DRAWINGS

The above and further features will be more clearly appreciated from the following detailed description when taken in conjunction with the accompanying drawings.

FIG. 1A-1B is a series of cartoons showing key events in cardiovascular disease. FIG. 1A is a cartoon showing key players in atherosclerosis, which is an inflammatory disease. Reproduced from Ross "Atherosclerosis—An inflammatory disease" N Engl J Med (1999) 340:115-126 and Libby "Current concepts of the pathogenesis of the acute coronary syndromes" Circulation (2001) 140:365-372. FIG. 1B is a schematic cartoon showing how oxidized phospholipids activate vascular wall macrophages, which leads to release of pro-inflammatory cytokines implicated in clinical events.

FIG. 2 is a schematic showing how subjects with a specific IL-1 genotype pattern (i.e., "positive" IL-1 genotype pattern) overproduce IL-1β when activated whereas subjects with the opposite IL-1 genotype pattern (i.e., a "negative" IL-1 genotype pattern) does not overproduce IL-1β when activated. 30-60% of human subjects, depending on ethnic/racial background, carry IL-1 genotype patterns that over produce IL-1β.

FIG. 3 is a series of graphs showing the link between risk for second CVD events and IL-1 genetic variants. FIG. 3, left panel, is a chart showing that Lipoprotein(a) risk for second cardiovascular disease (CVD) events is conditional on IL-1 genetic variations. FIG. 3, right panel, is a chart showing that oxidized phospholipids on apolipoprotein B-100 particles (OxPL/ApoB) risk for second CVD events is conditional on IL-1 genetic variations.

DETAILED DESCRIPTION OF THE INVENTION

Figure 1B:
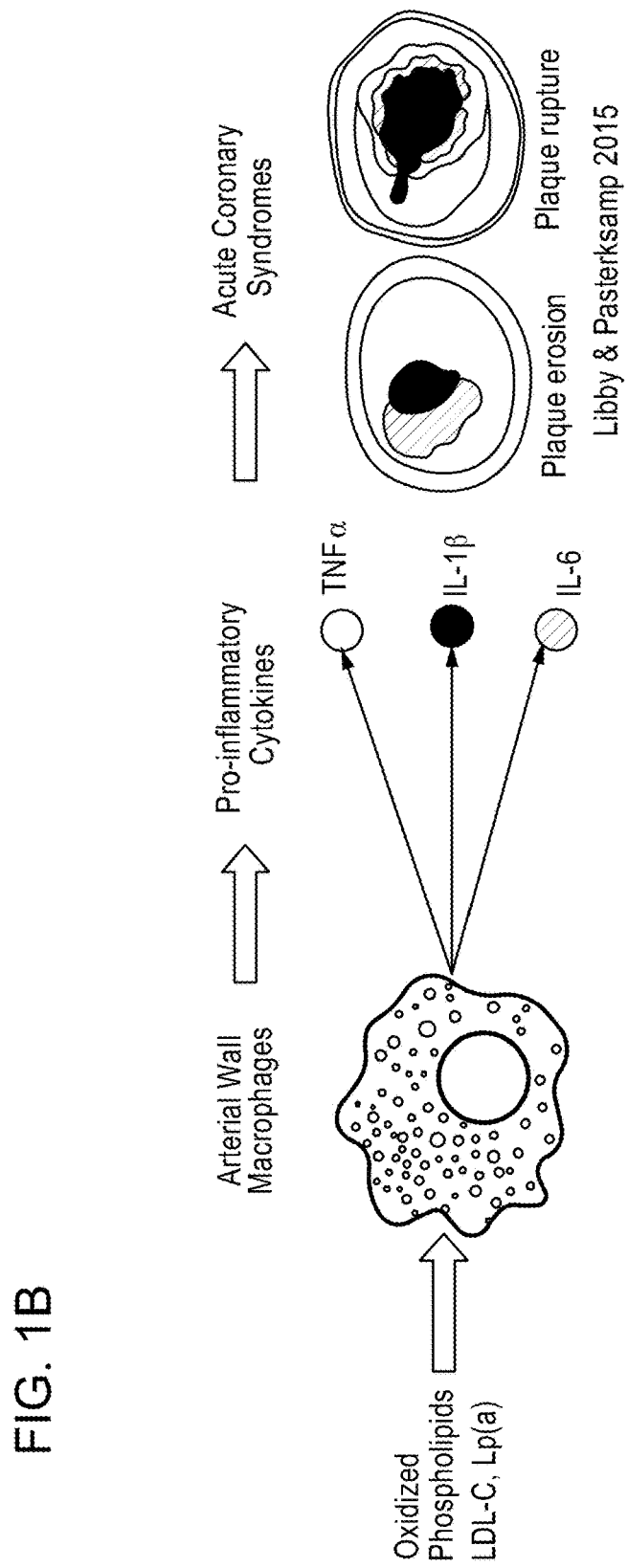
Figure 4:
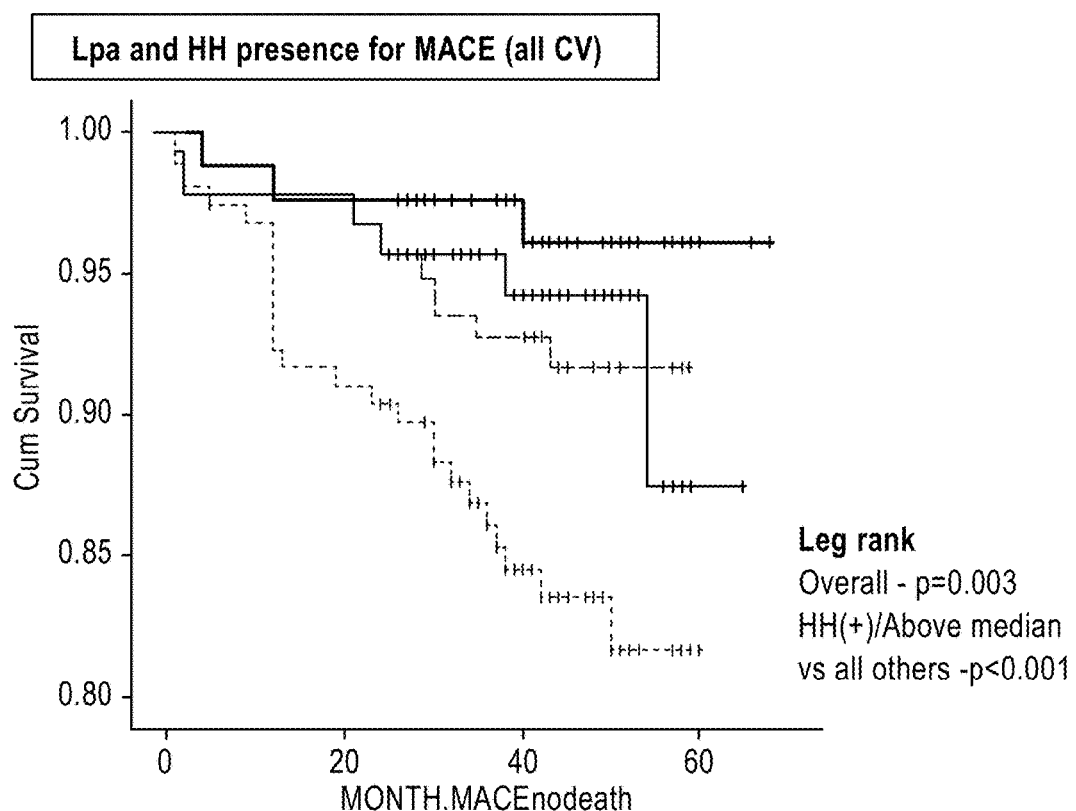
FIG. 4 is a chart showing that Lipoprotein(a) risk for major adverse cardiac events (MACE) is conditional on IL-1 genetic variations.

The present invention is based upon the discovery that specific IL-1 genotype patterns stratify individuals into groups relating to their member's likelihood of over-producing IL-1 and having an auto-inflammatory response in the vascular wall in response to one or more clinical indicator, including, but not limited to, Lp(a) levels, Triglyceride-rich lipoprotein levels, OxPL levels, LDL-C levels, CRP levels, and hypertension. Importantly, it was discovered that even with optimal LDL-C lowering, Lp (a) remains a risk factor to cardiovascular event in subjects having an IL-1 positive genotype.

Traditional risk factors are important in identifying persons at increased risk for cardiovascular disease (CVD) but do not fully explain global risk. For example, despite optimal secondary prevention strategies, including achieving very low LDL-C levels, significant residual CVD risk remains and most events are not prevented. Significant variability also exists in the clinical expression of CVD among persons with similar risk factors. Finally, a sizable proportion of CVD risk may be accounted for by low frequency but cumulative genetic variations that are not fully described or understood.

Based on a preponderance of epidemiological and genetic studies, Lp(a), whose plasma levels are primarily genetically determined, is now established as an independent, causal risk factor for CVD. Like other risk factors, Lp(a) has variable expression of CVD disease at different circulating level thresholds. Understanding the influences that modify the strength of risk factors may allow more rational and personalized therapy for patients at risk for CVD.

The present invention provides in part, an IL-1 genetic test in combination with Lp(a), for example, that predicts approximately 60% of recurrent cardiac events within the first two years of an initial event and intervention. The present invention enables cardiologists to increase monitoring of and/or provide more aggressive and optimal preventive interventions or treatments to specific subsets of patients. The IL-1 genetic test in combination with an clinical indicator has further utility in predicting a cardiac event in an individual not known to have previously had a cardiac event.

It has been discovered that individuals can be stratified into one of two IL-1 genotype patterns, i.e., Positive or Negative based upon their complex IL-1 genotype for three or five SNP loci. See, Table 1 and Table 2.

TABLE 1

| rs17561 +4845 | rs4848306 -3737 | rs1143623 -1464 | rs16944 5-11 | rs1143634 +3954 | IL-1 Pattern |
|---|---|---|---|---|---|
| T/‡ | †/† | G/G | C/C | T/† | Positive |
| G/G | †/† | G/G | C/C | †/† | Positive |
| ‡/‡ | †/† | G/G | C/C | C/C | Positive |
| T/‡ | C/† | G/G | C/T | T/† | Positive |
| G/G | C/† | G/G | C/T | †/† | Positive |
| ‡/‡ | C/† | G/G | C/T | C/C | Positive |
| T/‡ | C/C | C/G | C/T | T/† | Positive |
| G/G | C/C | C/G | C/T | †/† | Positive |
| ‡/‡ | C/C | C/G | C/T | C/C | Positive |
| T/‡ | C/T | C/G | C/T | T/† | Negative |
| G/G | C/T | C/G | C/T | †/† | Negative |
| ‡/‡ | C/T | C/G | C/T | C/C | Negative |
| T/‡ | C/C | G/G | T/T | T/† | Positive |
| G/G | C/C | G/G | T/T | †/† | Positive |
| ‡/‡ | C/C | G/G | T/T | C/C | Positive |
| T/‡ | C/C | C/* | T/T | T/† | Negative |
| G/G | C/C | C/* | T/T | †/† | Negative |
| ‡/‡ | C/C | C/* | T/T | C/C | Negative |

TABLE 2

| rs17561 +4845 | rs16944 -511 | rs1143634 +3954 | IL-1 Pattern |
|---|---|---|---|
| T/‡ | C/C | T/† | Positive |
| G/G | C/C | †/† | Positive |
| ‡/‡ | C/C | C/C | Positive |
| T/‡ | C/T | T/† | Positive |
| G/G | C/T | †/† | Negative |
| ‡/‡ | C/T | C/C | Negative |
| T/‡ | T/T | T/† | Negative |
| G/G | T/T | †/† | Negative |
| ‡/‡ | T/T | C/C | Negative |

In Table 1 and Table 2, "*" is G or C; "†" is C or T; and "‡" is G or T.

A subject having an uncommon complex IL-1 genotype not exemplified in Table 1 and Table 2 is considered herein as having an IL-1 genotype pattern of "Negative".

A subject may be stratified into an IL-1 genotype pattern by the SNP loci listed in Table 1 and Table 2 and/or SNP loci in linkage disequilibrium (LD), e.g., 80% LD, with the SNP loci listed in Table 1 and Table 2

A subject of certain racial/ethnic groups may be stratified into an IL-1 genotype pattern based upon five SNP loci listed in Table 1; other racial/ethnic groups may require three SNP loci (as in Table 2) to be stratified into an IL-1 genotype pattern. Differences in the frequencies or even the absence of a specific SNP of specific SNPs in certain racial/ethnic groups may require the inclusion of additional informative SNPs.

The present invention allows a diagnosis and optimal treatment recommendation for a subject based upon his/her IL-1 genotype pattern and status of one or more clinical indicators.

Accordingly, the invention features a method for predicting the risk of and preventing a future cardiac event in a human subject by obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus. If the subject is determined to have a positive or negative IL-1 genotype pattern (based on the information obtained and the information in Table 1 and Table 2 and has a total LDL-C plasma concentration of 70 mg/dL or less and/or a total Lp(a) plasma concentration of at least 5 mg/dL thus subject is administered an IL-beta inhibitor. The IL-beta inhibitor is for example canakinumab. Optionally, the method further includes administering one or more drugs from Table 4.

Additionally, the invention feature a method for determining whether a human subject would receive a therapeutic benefit from/would be responsive to IL-1 blocking drug and treating the subject by obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus. If the subject has a positive IL-1 pattern and a total LDL-C plasma concentration of 70 mg/dL or less and/or a total Lp(a) plasma concentration of at least 5 mg/dL; thus subject is administered an IL-1 blocking drug to the subject. The IL-1 blocking drug is for example canakinumab. Optionally, the method further includes administering one or more drugs from Table 4.

In a non-limiting example, if a subject has a Positive IL-1 genotype pattern and has a measured Lp(a) level (an exemplary clinical indicator) above a threshold value, the subject is administered an Lp(a) reducing drug and, optionally, is administered an Lp(a) reducing drug and an IL-1 lowering drug, but may also receive an IL-1 lowering drug without an Lp(a) reducing drug; whereas a subject who has a Positive IL-1 genotype pattern and has a measured Lp(a) level below a threshold value is not administered an Lp(a) reducing drug and, optionally, is administered an IL-1 lowering drug.

Similarly, if a subject has a Positive IL-1 genotype pattern and has a measured LDL-C level above a threshold value, then the subject is administered an LDL-C reducing drug, e.g., a statin, and, optionally, is administered an LDL-C reducing drug and an IL-1 lowering drug, whereas a subject who has a Positive IL-1 genotype pattern and has a measured LDL-C level below a threshold value is not administered an LDL-C reducing drug and, optionally, is administered an IL-1 lowering drug.

Additionally, when the clinical indicator is blood triglycerides, a subject who has a Positive IL-1 genotype pattern and high measured triglyceride levels above a threshold value, the subject is administered a triglyceride reducing drug and, optionally, is administered a triglyceride reducing drug and an IL-1 lowering drug, whereas a subject who has a Positive IL-1 genotype pattern and does not have high measured triglyceride levels is not administered a triglyceride reducing drug and, optionally, is administered an IL-1 lowering drug.

Moreover, when the clinical indicator is blood pressure, a subject who has a Positive IL-1 genotype pattern and high blood pressure (above a threshold value), the subject is administered a blood pressure reducing drug and, optionally, is administered a blood pressure reducing drug and an IL-1 lowering drug, whereas a subject who has a Positive IL-1 genotype pattern and does not have high blood pressure is not administered a blood pressure reducing drug and, optionally, is administered an IL-1 lowering drug.

When the clinical indicator is CRP, a subject who has a Positive IL-1 genotype pattern and high CRP levels (above a threshold value), the subject is administered a CRP reducing drug and, optionally, is administered a CRP reducing drug and an IL-1 lowering drug, whereas a subject who has a Positive IL-1 genotype pattern and does not have high CRP is not administered a CRP reducing drug and, optionally, is administered an IL-1 lowering drug.

When the clinical indicator is OxPL levels, a subject who has a Positive IL-1 genotype pattern and high OxPL levels (above a threshold value), the subject is administered a OxPL reducing drug and, optionally, is administered a OxPL reducing drug and an IL-1 lowering drug, whereas a subject who has a Positive IL-1 genotype pattern and does not have high OxPL is not administered a OxPL reducing drug and, optionally, is administered an IL-1 lowering drug.

Alternately, if a subject has a Positive IL-1 genotype pattern and more than one measured clinical indicator at each marker's threshold, the subject is administered a first drug that reduces levels of the first clinical indicator and a second drug that reduces levels of the second clinical indicator and, optionally, is administered the first drug that reduces levels of the first clinical indicator, the second drug that reduces levels of the second clinical indicator, and an IL-1 lowering drug.

Levels of more than one clinical indicator may be reduced by a single drug; in these cases, the subject with Positive IL-1 genotype pattern and more than one measured clinical indicator at each marker's threshold is administered the single drug that reduces levels of more than one clinical indicator, and, optionally, is administered the single drug that reduces levels of more than one clinical indicator and an IL-1 lowering drug.

The threshold value for a clinical indicator depends on the particular clinical indicator measured. For example, the threshold value for Lp(a) may be 5 mg/dL or more, 10 mg/dL or more, 20 mg/dL or more, 30 mg/dL or more, 50 mg/dL or more; 60 mg/dL or more, 70 mg/dL, 80 mg/dL or more, or 90 mg/dL or more. The threshold value for Lp(a) may be 5 mg/dL or more. Alternatively, the threshold value for Lp(a) may be 5 mg/dL or less, 10 mg/dL or less, 20 mg/dL or less, 30 mg/dL or more, 50 mg/dL or less; 60 mg/dL or less, 70 mg/dL, 80 mg/dL or less, or 90 mg/dL or less.

The threshold value of LDL-C may be 25 mg/dL or more, 50 mg/dL or more, 60 mg/dL or more, 70 mg/dL or more, 80 mg/dL or more, 90 mg/dL or more, 100 mg/dL or more, 110 mg/dL or more, 120 mg/dL or more, 150 mg/dL or more, 160 mg/dL or more, 170 mg/dL or more, 180 mg/dL or more, 190 mg/dL or more. Alternatively, the threshold value of LDL-C may be 25 mg/dL or less, 50 mg/dL or less, 60 mg/dL or less, 70 mg/dL or less, 80 mg/dL or less, 90 mg/dL or less The threshold value for triglycerides may be 500 mg/dL or more, 400 mg/dL or more, 300 mg/dL or more, 200 mg/dL or more; 190 mg/dL or more, 180 mg/dL or more, 170 mg/dL or more, 160 mg/dL or more, 150 mg/dL or more, 140 mg/dL or more, or 130 mg/dL or more. Alternatively, the threshold value for triglycerides may be 500 mg/dL or less, 400 mg/dL or less, 300 mg/dL or less, 200 mg/dL or less; 190 mg/dL or less, 180 mg/dL or less, 170 mg/dL or less, 160 mg/dL or less, 150 mg/dL or less, 140 mg/dL or less, or 130 mg/dL or less, 120 mg/dL or less, 110 mg/dL or less, 100 mg/dL or less, or 90 mg/dL or less.

The threshold value for high blood pressure may be 140/90 or more; or 120/80 or more. Alternatively, the threshold value for high blood pressure may be 140/90 or less; or 120/80 or less.

A threshold value for CRP may be 20 mg/L or more, 15 mg/L or more 10 mg/L or more, 7.5 mg/L or more, 5 mg/L or more, or 2.5 mg/L or more. Alternatively, the CRP may be 20 mg/L or less, 15 mg/L or less, 10 mg/L or less, 7.5 mg/L or less, 5 mg/L or less, or 2.5 mg/L or less.

The threshold value for a clinical indicator may vary for an individual based upon other levels of other clinical indicators and/or other CVD risk predictors, e.g., sex, age, height, weight, previous history of a heart attack and/or the presence of other metabolic disorders, e.g., Type II diabetes. Thus, depending on the these, and other, factors, a threshold value for a clinical indicator may be reduced by 1%, 5%, 10%, 20%, 30%, 40%, 50% or any percentage in between; alternately, depending on the these, and other, factors, a threshold value for a clinical indicator may be increased by 1%, 5%, 10%, 20%, 30%, 40%, 50% or any percentage in between.

The present invention, in view of the disclosures of Table 1 and Table 2, allows a skilled artisan to identify:
Subjects likely to derive more benefit from specific drug;
Subjects with one IL-1 genotype pattern who may respond favorably to lower levels of the drug than subjects of a different pattern;
Subjects who should be on an IL-1-blocking drug earlier than others because their genotype pattern is more aggressive; and
Subjects with an IL-1 dominant disease subtype that may be predictably responsive to IL-1-blocking drugs but not other agents which have different modes of action.

Modulators of IL-1 biological activity (e.g., IL-1α, IL-1β, or IL-1 receptor antagonist) or a protein encoded by a gene that is in linkage disequilibrium with an IL-1 gene, can comprise any type of compound, including a protein, peptide, peptidomimetic, lipid, small molecule, or nucleic acid. A modulator may be a botanical or extract of a botanical.

A modulator may indirectly act upon an IL-1 gene in that the modulator activates or represses a gene or protein that, in turn or ultimately, acts upon the IL-1 gene. As used herein, the term "ultimately" is meant that the modulator acts upon a first gene or protein and the first gene or protein directly acts upon the IL-1 gene or the first gene or protein acts upon a second gene or protein which directly (or indirectly) acts upon the IL-1 gene. Such indirect gene regulation is well known in the art. A modulator that acts upstream to the IL-1 gene is useful in the present invention. An example of a modulator that acts upstream of the IL-1 gene is Aldeyra's NS2 compound which traps excess free aldehydes, which are known to activate a number of intracellular inflammatory factors including NF-kB, a prominent protein in the inflammatory response. Another example of that acts upstream of the IL-1 gene is Ionis Pharmaceutical's IONIS-APO(a)-$L_{Rx}$ and Arrowhead's ARC-LPA, which reduces Lp(a) levels that would be expected to activate arterial wall macrophages to produce IL-1β.

Alternately, a modulator may act downstream of the IL-1 gene by directly or indirectly affecting a gene or protein that operates in parallel to IL-1 in an inflammatory cascade.

An agonist can be a protein or derivative thereof having at least one bioactivity of the wild-type protein, e.g., receptor binding activity. An agonist can also be a compound that upregulates expression of a gene or which increases at least one bioactivity of a protein. An agonist can also be a compound which increases the interaction of a polypeptide with another molecule, e.g., a receptor.

An antagonist can be a compound which inhibits or decreases the interaction between a protein and another molecule, e.g., blocking the binding to receptor, blocking signal transduction, and preventing post-translation processing (e.g., IL-1 converting enzyme (ICE) inhibitor). An antagonist can also be a compound that downregulates expression of a gene or which reduces the amount of a protein present. The antagonist can be a dominant negative form of a polypeptide, e.g., a form of a polypeptide which is capable of interacting with a target. Antagonists, include nucleic acids (e.g., single (antisense) or double stranded (triplex) DNA or PNA and ribozymes), protein (e.g., antibodies) and small molecules that act to suppress or inhibit IL-1 transcription and/or protein activity.

An anti-inflammatory drug refers to any agent or therapeutic regimen (including a pharmaceutical, biologic, nutraceutical, and botanical) that prevents or postpones the development of or alleviates a symptom of the particular disease, disorder, or condition that involved an inflammatory process in the subject. The drug can be a polypeptide, peptidomimetic, nucleic acid or other inorganic or organic molecule, a "small molecule," vitamin, mineral, or other nutrient. The drug modulates the production of the active IL-1β or IL-11α polypeptides, or at least one activity of an IL-1 polypeptide, e.g., interaction with a receptor, by mimicking or potentiating (agonizing) or inhibiting (antagonizing) the effects of a naturally-occurring polypeptide. An anti-inflammatory drug also includes, but is not limited to, anti-cholesterol drugs (e.g., statins), diabetes mellitus drugs, drugs that treat acute syndromes of the heart and vascular system (e.g., a cardiovascular disease), and arthritis.

Non-limiting examples of anti-inflammatory drugs that modulate IL-1 biological activity useful in the present invention are listed in Table 3. These drugs generally have a mode of action that includes modulation of IL-1 gene expression, modulation of inflammasomes, IL-1 receptor blocking agents, agents that bind IL-1β or IL-1α to inhibit attachment to the active receptor. IL-1 blocking drugs may also indirectly target IL-1 by blocking key activators of IL-1 gene expression.

TABLE 3

| | |
|---|---|
| ABT -981 | Gevokizumab |
| AC-701 | Givinostat |
| Ammonium trichloro-tellurate | Isunakinra |
| Anakinra | Rilonacept |
| Anakinra Biosimilar | RON-2315 |
| APX-002 | Sairei-To |
| Binimetinib | SER-140 |
| Can-04 | Tadekinig-alpha |
| Canakinumab | Xilonix |

TABLE 3-continued

| | |
|---|---|
| Diacerein | XL-130 |
| DLX-2681 | NUTRILITE ® IL1 Heart Health Nutrigenomic Dietary Supplement |

Twenty percent of the general population has elevated Lp(a), an LDL-like particle which may be more atherogenic than LDL cholesterol. Unfortunately, elevated Lp(a) levels do not generally respond to statin drugs or to diet modifications. Lp(a) levels are reduced by niacin in those who can tolerate the side effects.

Non-limiting examples of Lp(a) reducing drugs useful in the present invention are listed in Table 4:

TABLE 4

| | |
|---|---|
| PCSK9 inhibitor Repatha (Amgen) | ARC-LPA (Arrowheas) |
| PCSK9 inhibitor Pralvent | |
| Alirocumab (Regeneron) | |
| APO(a)-$L_{RX}$ (Ionis) | |

Non-limiting examples of anti-cholesterol drugs useful in the present invention are listed in Table 5:

TABLE 5

| | |
|---|---|
| Advicor | Pitavastatin (Livalo) |
| alirocumab | Lofibra |
| lovastatin (Altoprev and Mevacor) | niacin |
| amlodipine-atorvastatin | niacin-lovastatin |
| Antara | niacin-simvastatin |
| atorvastatin | Niacor |
| Caduet | Niaspan |
| cholestyramine | Praluent |
| Colestid | Pravastatin (Pravachol) |
| colestipol | Prevalite |
| rosuvastatin (Crestor) | Questran |
| Endur-Acin | Light |
| evolocumab | Questran |
| ezetimibe | Repatha SureClick |
| ezetimibe-simvastatin | Repatha Syringe |
| fenofibrate | Simcor |
| fenofibric acid (choline) | simvastatin (Zocor) |
| fenofibric acid | Slo-Niacin |
| Fenoglide | Tricor |
| Fibricor | Triglide |
| fluvastatin | Trilipix |
| fluvastatin (Lescol and Lescol XL) | Vytorin |
| atorvastatin (Lipitor) | Zetia |
| Lipofen | |

Non-limiting examples of anti-Triglyceride-rich lipoproteins drugs useful in the present invention are listed in Table 6:

TABLE 6

| |
|---|
| fibrates (fenofibrate and gemfibrozil) |
| niacin |
| omega-3 fatty acids |
| Volanesorsen |
| Alipogene tiparvovec (Glybera) |
| Lomitapide |

Non-limiting examples of blood pressure reducing drugs useful in the present invention are listed in Table 8:

TABLE 7

| | |
|---|---|
| diuretics | Altace |
| Vasotec | Prinivil |
| Norvasc | Diovan |

TABLE 7-continued

| | |
|---|---|
| Procardia | Cozaar |
| Tenormin | Tiazac |
| Tekturna | Adalat CC |
| Afeditab CR | Cardizem |
| Lopressor | Corgard |
| Toprol-XL | |

Non-limiting examples of diabetes mellitus drugs include: acarbose, ActoplusMET, Actos, Amaryl, Avandamet, Avandia, bromocriptine, Bydureon, Byetta, Farxiga, Fortamet, glimepiride, glipizide, Glucophage, GlucophageXR, Glucovance, Glumetza, glyburide, Humalog, Invokana, Janumet, Januvia, Kombiglyze XR, Lantus, Lantus Solostar, Levemir, metformin, Novolog, NovologFlexpen, Novolog Mix70-30FlexPen, Onglyza, Parlodel, pioglitazone, Prandin, Starlix, Tradjenta, Victoza2-Pak, and WelChol.

Non-limiting examples of drugs that treat acute syndromes of the heart and vascular system include: Altace, Arixtra metoprolol tartrate, aspirin, atenolol, Bystolic, BRILINTA, carvedilol, clopidogrel, Coreg, Coumadin, diovan, enoxaparin, heparin, Lisinopril, Lopressor, Lovaza, Lovenox, metoprolol tartrate, Niaspan, Nitro-Bid, nitroglycerin, Plavix, Ramipril, and warfarin.

Any of the drugs listed in Table 3 to Table 7 (alone or together) may be used in the present invention. An individual may be administered one or more drugs of Table 3 to Table 7 at a higher dose or at a lower dose (e.g., the dose of a single treatment and/or a daily dose comprising one or more single treatments) depending on his/her IL-1 genotype pattern and status of one or more clinical indicators; alternately, the individual may be not given the particular drug depending on his/her IL-1 genotype pattern and status of one or more clinical indicators and instead may be administered a different drug. For example, rather than being administered Xilonix, which is a human monoclonal antibody against IL-1α, based on the individual's IL-1 genotype pattern and clinical indicator status, the individual may be administered Gevokizumab, which is a human monoclonal antibody against IL-1β.

Additionally, drugs other than those listed in Table 3 to Table 7 may be used in the present invention. For this, an alternate drug having a mode of action (MOA) similar to or identical to a drug listed in Table 3 to Table 7 may be provided instead of or in addition to the drug listed in Table 3 to Table 7. One skilled in the art is able to determine alternate drugs that are useful in the present invention.

A subject may be administered one or more drugs from Table 3 to Table 7 or one or more alternate drugs having a MOA similar to or identical to a drug listed in Table 3 to Table 7 at the standard therapeutic dose. A drug may be given at a dose lower than the standard therapeutic dose, e.g., 99%, 95%, 90%, 85%, 80%, 75%, 70%, 60%, 50%, 40%, 30%, 20%, 15%, 10%, or 5%, and any percentage in between lower than the standard therapeutic dose. A drug may be given at a dose higher than the standard therapeutic dose, e.g., 5%, 10%, 15%, 20%, 30%, 40%, 50%, 60%, 70%, 75%, 80%, 85%, 90%, 95%, 100%, 125%, 150%, 175%, 200%, 300%, 400%, 500%, 600%, 700%, 800%, 900%, 1000%, 2000%, or more, and any percentage in between higher than the standard therapeutic dose. For example, if a standard therapeutic dose is 10 mg per day, a subject may be given 7 mg per day as a lower than standard therapeutic dose or 13 mg per day as a higher than standard therapeutic dose.

A subject in need of treatment for a CVD or at risk for CVD will provide or has provided a biological sample comprising a nucleic acid and comprising at least one clinical indicator; alternately, when blood pressure is the clinical indicator, the subject will provide or has provided a biological sample comprising a nucleic acid and has his/her blood pressure measured. Single nucleotide polymorphism (SNP) alleles in the isolated nucleic acid for each of the, at least 3, or 5 polymorphic loci identified in Table 1 and Table 2, or polymorphic loci in linkage disequilibrium to the polymorphic loci identified in Table 1 and Table 2 will be detected by any method known in the art and a composite IL-1 genotype will be determined. From the determined composite IL-1 genotype, a Positive or Negative IL-1 genotype pattern will be determined based on the information disclosed in Table 1 and Table 2. At least one of the subject's clinical indicators will be measured. When the subject has a Positive IL-1 genotype pattern and has a measured clinical indicator above a threshold level, s/he will be administered one or more drugs identified in Table 3 to Table 7, or alternately, be administered one or more drugs identified in Table 3 to Table 7 and one or more drug identified in Table 3. When the subject has a Positive IL-1 genotype pattern and has a measured clinical indicator below a threshold level, s/he will not be administered a drug identified in Table 4 to Table 7, or alternately, will be administered more drug identified in Table 3. The present invention further includes use of alternate drugs to the drugs listed in Table 3 to Table 7.

A drug may be useful in the present invention for more than one disease or disorder relevant to the present invention.

Any drug of Table 3 to Table 7 may be administered with any other drug or drugs of Table 3 to Table 7.

Any drug of Table 3 to Table 7 may be administered with any other drug or drugs known in the art that is capable of treating or reducing a symptom of one or more disease or disorder relevant to the present invention.

A drug is prepared depending in its route of drug administration. Examples of drug administration routes that are useful in the present invention are described on the U.S. Food and Drug Administration's website at the World Wide Web (www.fda.gov/Drugs/DevelopmentApprovalProcess/FormsSubmissionRequirements/ElectronicSubmissions/DataStandardsManualmonographs/ucm071667.htm).

Preparations for oral administration generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as ethylenediaminetetraacetic acid (EDTA); a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art. Topical ocular formulations, e.g., eye drops and eye ointments, are considered.

The amount of agent that is administered to the subject can and will vary depending upon the type of agent, the subject, and the particular mode of administration. Those skilled in the art will appreciate that dosages may also be determined with guidance from Goodman & Gilman's The Pharmacological Basis of Therapeutics, Twelfth Edition (2011), Appendix II, pp. 1891-1991, and the Physicians' Desk Reference 70$^{th}$ Edition, 2016.

Pharmacogenomics

Pharmacogenomics is the methodology which associates genetic variability with physiological and clinical responses to a drug. Pharmacogenetics is a subset of pharmacogenomics and is defined as "the study of variations in DNA sequence as related to drug response" (ICH E15; see the World Wide Web www.fda.gov/downloads/RegulatoryInformation/Guidances/ucm129296.pdf). Pharmacogenetics often focuses on genetic polymorphisms in genes related to drug metabolism, drug mechanism of action, underlying disease type, and drug associated side effects. Pharmacogenetics is the cornerstone of Personalized Medicine which allows the development and the targeted use of drug therapies to obtain effective and safe treatment, as well as to adjust existing treatment regimens to further optimize the efficacy and safety profile for the individual patient.

Pharmacogenetics has become a core component of many drug development programs, being used to explain variability in drug response among subjects in clinical trials, to address unexpected emerging clinical issues, such as adverse events, to determine eligibility for a clinical trial (pre-screening) to optimize trial yield, to develop drug companion diagnostic tests to identify patients who are more likely or less likely to benefit from treatment or who may be at risk of adverse events, to provide information in drug labels to guide physician treatment decisions, to better understand the mechanism of action or metabolism of new and existing drugs, and to provide better understanding of disease mechanisms as associated with treatment response.

Generally, pharmacogenetics analyses are often performed using the candidate genes research technique, which is a hypothesis-driven approach, based on the detection of polymorphisms in candidate genes pre-selected using knowledge of the disease, the drug's mode of action, toxicology, or metabolism of the drug.

Cardiovascular Disease Types and Causes

Cardiovascular disease, e.g., acute coronary events such as myocardial infarction and stroke, is a class of disease that involves the heart and/or the blood vessels including the arteries and the veins. In the Western world, cardiovascular disease, typically associated with underlying atherosclerosis, is the leading cause of death (Martin-Ventura et al., 2009, Rev. Esp. Cardiol 62i6:677-688. citing Murray and Lopez, 1997, Lancet 349:1269-1276).

However, cardiovascular mortality in developed countries has decreased sharply in recent decades (Tunstall-Pedoe, H., et al., Estimation of contribution of changes in coronary care to improving survival, event rates, and coronary heart disease mortality across the WHO MONICA Project populations. Lancet, 2000. 355(9205): p. 688-700). This is likely due to the development and use of efficacious hypertension, thrombolytic, and lipid lowering therapies (Kuulasmaa, K., et al., Estimation of contribution of changes in classic risk factors to trends in coronary-event rates across the WHO MONICA Project). Nevertheless, cardiovascular diseases remain the major cause of death in industrialized countries, at least in part due to the presence of highly prevalent risk factors and insufficient treatment (Wong, M. D., et al., Contribution of major diseases to disparities in mortality. N Engl J Med, 2002. 347(20): p. 1585-92). Even with appropriate therapy, not all patients respond equally well to treatment. For example, despite the overwhelming evidence that statins decrease risk for cardiovascular disease, both in primary and secondary intervention settings, statin therapy clearly only achieves partial risk reduction. While a decrease in risk of 23 to 37% seen in the above trials is substantial and extremely important clinically, the majority of events still are not prevented by statin treatment. This is not surprising given the complexity of cardiovascular disease etiology, which is influenced by genetics, family history, environment, and a variety of additional risk factors including dyslipidemia, elevated cholesterol, age, gender, hypertension, diabetes, obesity, and smoking.

It is reasonable to assume that all of these multi-factorial risks modify drug responses and determine the final benefit that each individual achieves from therapy. Furthermore, with the increasing incidence of Type 2 diabetes and obesity in Western countries (Flegal, K. M., et al., Prevalence and trends in obesity among US adults, 1999-2000. Jama, 2002. 288(14): p. 1723-7, Boyle, J. P., et al., Projection of diabetes burden through 2050: impact of changing demography and disease prevalence in the U.S. Diabetes Care, 2001. 24(11): p. 1936-40), which are two major risk factors for coronary artery disease, and the emergence of greater cardiovascular risk factors in the developing world (Yusuf, S., et al., Global burden of cardiovascular diseases: Part II: variations in cardiovascular disease by specific ethnic groups and geographic regions and prevention strategies. Circulation, 2001. 104(23): p. 2855-64, Yusuf, S., et al Global burden of cardiovascular diseases: part I: general considerations, the epidemiologic transition, risk factors, and impact of urbanization. Circulation, 2001. 104(22): p. 2746-53), the need for ever more effective treatment of cardiovascular disease is predicted to steadily increase.

Atherosclerosis is a chronic disease process characterized by lipid deposits and fibrosis of the intima, irregularly distributed in large and medium sized arteries. The disease is progressive and most often becomes clinically manifest in the middle-aged and elderly. When severe, the atherosclerotic plaque causes a reduction of the cross-sectional area of the arterial lumen, with and without thrombosis. Atherosclerotic plaques can occur in essentially any or all of the blood vessels of the body, resulting in cardiovascular diseases involving the heart (e.g., acute coronary syndrome, heart failure, and myocardial infarction), the brain (e.g., stroke, transient ischemic attack, and brain infarction), the kidney (e.g., acute and chronic kidney disease, hypertension), and the extremities (e.g., peripheral vascular disease, lower and/or upper extremity claudication, and lower and/or upper extremity ischemia). Resultant ischemic manifestations include: angina pectoris, rayocardial infarction, stroke, intermittent claudication, gangrene of the lower extremities, and renovascular hypertension.

Atherosclerosis may be considered as an aberrant form of wound-healing in arteries.

Atherosclerosis is considered by many to be an inflammatory disease. In particular, the lesions of atherosclerosis appear to represent a series of highly-specific cellular and molecular responses that can be described as an inflammatory disease. See, e.g., Ross, "Atherosclerosis—An inflammatory disease" N Engl J Med (1999), 340:115-126; the publications cited in Ross (1999); and subsequent publications that cite Ross (1999); each of which is incorporated herein in reference in its entirety.

A number of technologies have been developed to identify patients at high risk for an adverse cardiac event. Coronary angiography has been considered the "gold standard" but is invasive, costly, and subject to operator-dependent variability (Sharma et al., 2010, Vase. Health Risk Manag. 6:307-316). Other, less invasive options being explored include coronary computed tomographic angiography (Sharma et al., supra; Cury et al., 2008. J. Nucl. Cardiol. 15 (4): 564-575). biomarkers (e.g., Martin-Ventura et al., 2009, Rev. Esp. Cardiol 62(6):677-688), adenosine stress magnetic resonance (Ingkanisorn et al., 2006, J. Am. Coll. Cardiol. 47(7): 1427-1432). the use of clinical predictors (Tadros et al., 2003. South Med. J. 96(1 Γ):1113-1120; Schillinger et al., 2004, Wien Klin. Wochenschr. 116(3): 83-89), and indicators of platelet activity (Marcucci et al., 2009, Circulation 119:237-242 (originally published online Dec. 31, 2008); Selvaraj et al., 2004, J. Throm. Thrombolysis 18(2): 109-115). Any of the above-mentioned technologies can be combined with the present invention for diagnostic and treatment purposes of a subject with or suspected of having cardiovascular disease.

Clinical Indicators

In the present invention, using the candidate genes research technique, a subject has his/her composite IL-1 genotype or IL-1 genotype pattern determined (as disclosed herein). Additionally, s/he will have levels of one or more clinical indicators measured. Non-limiting examples of the clinical indicators, include levels of Lp(a), OxPL, triglyceride-rich lipoproteins, LDL-C, and CRP.

Based on the combination of which clinical indicators are elevated and the subject's IL-1 genotype pattern a more aggressive and optimal therapeutic intervention will be determined.

An individual may be administered a higher dose or a lower dose (e.g., the dose of a single treatment and/or a daily dose comprising one or more single treatments) of a particular drug depending on his/her composite IL-1 genotype or IL-1 genotype pattern; alternately, the individual may be not given the particular drug depending on his/her composite IL-1 genotype or IL-1 genotype pattern and instead may be administered another drug. For example, the other drug may operate by a different mode of action.

Alternately, the present invention may be used to optimize the size of a clinical trial.

For this, a study population is stratified by IL-1 pattern during or before randomization. This way, each group in a study will have sufficient numbers of members from each Pattern. This allows for smaller-sized groups which can nonetheless be informative and provide statistical significance. Non-Caucasian ethnic/racial groups have different frequencies for each pattern; thus, study populations comprising Non-Caucasians may need to have their total population size adjusted accordingly.

Such stratification of clinical trial subjects may occur any time before, during, or after the clinical trial. In the latter case, for example, if a clinical trial does not provide statistical significance using a general, non-stratified population, true statistical significant may be later be discovered when the subject data is reconsidered and stratified by IL-1 pattern. That is, if the data of the clinical did not show statistical evidence of a treatment response, the data could later be reevaluated with consideration of IL-1 patterns. If so, it is possible that a previously "unsuccessful" clinical trial could be made "successful" when subjects are retroactively stratified by CIL-1 pattern.

When subjects are stratified by IL-1 pattern, subjects of certain Patterns who will benefit from the treatment are identified and subjects of other Patterns who will not benefit (or benefit less) from the treatment are identified. Once the treatment is approved for clinical use, the stratified clinical trials will have revealed which patient populations (i.e., patients with a specific IL-1 pattern) should be provided the treatment and which patients should not.

Difference Between the Present Invention and U.S. Pat. No. 6,210,877

U.S. Pat. No. 6,210,877, which is incorporated herein by reference in its entirety, relates to methods for diagnosing CVD using only complex IL-1 genotypes. On the other hand, the present invention relates to diagnosing and optimally treating a subject based upon a composite IL-1 genotype or IL-1 genotype pattern and status of one or more clinical indicators. More specifically the present application is based upon that there are certain activators that have a major causative effect on atherosclerotic cardiovascular disease by activating inflammatory cytokines, but the disease only reaches a level of clinical impact if the IL-1 genotypes amplify the inflammation to a magnitude that causes clinically significant damage. The disease therefore requires both an activator, such as Lp(a), and the pro-inflammatory genotype. Given cost and potential adverse events of drugs targeting the activators, the drug clinical value is conditional on the IL-1 genotype or a drug that reduces the IL-1 amplification.

Ex Vivo Diagnostics

In aspects of the present invention, IL-1 levels can be measured ex vivo and in response to treatment with a therapeutic compound. For this, lymphocytes will be obtained from a subject. The lymphocytes will be treated with an IL-1 activator and then IL-1 levels (protein and/or mRNA) will be measured. If the lymphocytes produce increased IL-1 and to a critical level, then a diagnosis of the subject can be made and a prediction regarding an optimal treatment can be determined.

Isolated Nucleic Acid Molecules

As used herein, an "isolated nucleic acid molecule" generally is one that contains one or more of the SNPs disclosed herein or one that hybridizes to such molecule such as a nucleic acid with a complementary sequence, and is separated from most other nucleic acids present in the natural source of the nucleic acid molecule. As used herein, "a non-naturally occurring nucleic acid molecule" generally is one that contains one or more of the SNPs disclosed herein or one that hybridizes to such a molecule, such as a nucleic acid with a complementary sequence, but which does not correspond to a naturally occurring molecule, e.g., it can be a molecule prepared by recombinant nucleic acid technology, chemical synthesis, or other synthetic means such as polymerase chain reaction (PCR), and/or a nucleic acid which comprises one or more synthetic components such as a non-natural nucleotide or an added tag/motif.

The isolated nucleic acid may be obtained from any bodily fluid (such as blood, serum, plasma, urine, saliva, phlegm, gastric juices, semen, tears, sweat, etc.), skin, hair, cell (especially nucleated cells), biopsy, buccal swab, tissue, or tumor specimen. Alternately, the isolated nucleic acid may be amplified or synthesized from a nucleic acid obtained from any bodily fluid, skin, hair, cell, biopsy, buccal swab, tissue, or tumor specimen.

Generally, an isolated SNP-containing nucleic acid molecule includes one or more of SNPs and/or one or more SNPs in linkage disequilibrium with one or more SNPs. The isolated SNP-containing nucleic acid molecule may include flanking nucleotide sequences on either side of the SNP position. A flanking sequence can include nucleotide residues that are naturally associated with the SNP site and/or heterologous nucleotide sequences. Preferably, the flanking sequence is up to about 10,000, 1,000, 500, 300, 100, 60, 50, 30, 25, 20, 15, 10, 8, or 4 nucleotides (or any other length in-between) on either side of a SNP position, or as long as the full-length gene, entire protein-coding sequence (or any portion thereof such as an exon), entire enhancer/promoter region or portion thereof, or entire intron or portion thereof.

An isolated SNP-containing nucleic acid molecule can include, for example, a full-length gene or transcript, such as a gene isolated from genomic DNA (e.g., by cloning or PCR amplification), a cDNA molecule, or an mRNA transcript molecule.

An isolated nucleic acid molecule of the disclosed subject matter further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195 and 4,683,202; PCR Technology: Principles and Applications for DNA Amplification, ed. H. A. Erlich, Freeman Press, NY, N.Y. (1992)), ligase chain reaction (LCR) (Wu and Wallace, Genomics 4:560 (1989); Landegren et al., Science 241:1077 (1988)), strand displacement amplification (SDA) (U.S. Pat. Nos. 5,270,184 and 5,422,252), transcription-mediated amplification (TMA) (U.S. Pat. No. 5,399,491), linked linear amplification (LLA) (U.S. Pat. No. 6,027,923) and the like, and isothermal amplification methods such as nucleic acid sequence based amplification (NASBA) and self-sustained sequence replication (Guatelli et al., Proc Natl Acad Sci USA 87:1874 (1990)). Based on such methodologies, a person skilled in the art can readily design primers in any suitable regions 5' and 3' to a SNP disclosed herein. Such primers may be used to amplify DNA of any length so long that it contains the SNP of interest in its sequence.

The isolated nucleic acid molecules that include, consist of, or consist essentially of one or more polynucleotide sequences that contain one or more SNPs disclosed herein, complements thereof, SNPs in linkage disequilibrium with the SNPs disclosed herein, and/or SNP-containing fragments thereof. Non-limiting examples of SNPs in linkage disequilibrium with the SNPs disclosed herein include those listed in the Table below.

| SNP | Common | Linkage SNP | Rsquared |
|---|---|---|---|
| rs16944 | B(−511) | rs1143627 | 0.965 |
|  |  | rs13013349 | 0.964 |
|  |  | rs1143623 | 0.827 |
| rs1143623 | B(−1464) | rs12621220 | 0.963 |
|  |  | rs1143627 | 0.864 |
|  |  | rs13008855 | 0.857 |
|  |  | rs16944 | 0.827 |
|  |  | rs12053091 | 0.824 |
| rs484306 | B(−3737) | None |  |
| rs17561 | A(+4845) | rs3783557 | 0.961 |
|  |  | rs11898680 | 0.821 |
|  | A(−889) | rs1800587 |  |
| rs1143634 | B(+3954) | rs3917373 | 0.881 |

Isolated nucleic acid molecules can be in the form of RNA, such as mRNA, or in the form DNA, including cDNA and genomic DNA, which may be obtained, for example, by molecular cloning or produced by chemical synthetic techniques or by a combination thereof. Sambrook and Russell, Molecular Cloning: A Laboratory Manual, Cold Spring Harbor Press, N.Y. (2000). Furthermore, isolated nucleic acid molecules, particularly SNP detection reagents such as probes and primers, can also be partially or completely in the form of one or more types of nucleic acid analogs, such as peptide nucleic acid (PNA). U.S. Pat. Nos. 5,539,082; 5,527,675; 5,623,049; and 5,714,331. The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art. See, e.g., Corey, "Peptide nucleic acids: expanding the scope of nucleic acid recognition," Trends Biotechnol 15 (6):224-9 (June 1997), and Hyrup et al., "Peptide nucleic acids (PNA): synthesis, properties and potential applications," Bioorg Med Chem 4 (1):5-23 (January 1996). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System and the sequence information provided herein.

The isolated SNP-containing nucleic acid molecule may comprise modified, synthetic, or non-naturally occurring nucleotides or structural elements or other alternative/modified nucleic acid chemistries known in the art. Such nucleic acid analogs are useful, for example, as detection reagents (e.g., primers/probes) for detecting the SNPs identified herein. Furthermore, kits/systems (such as beads, arrays, etc.) that include these analogs are also encompassed herein.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, Cold Spring Harbor Laboratory (2001); DNA Cloning, Volumes I and II (P. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. Q. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu at al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

SNP Detection Reagents

In aspects of the present invention, each of the one or more of the SNPs disclosed herein can be used for the design of SNP detection reagents. As used herein, a "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a non-naturally occurring nucleic acid probe that hybridizes to a target nucleic acid containing one of the SNPs disclosed herein. In a preferred embodiment, such a probe can differentiate between nucleic acids having a particular nucleotide (allele) at the target SNP position from other nucleic acids that have a different nucleotide at the same target SNP position. In addition, a detection reagent may hybridize to a specific region 5' and/or 3' to the SNP position.

Another example of a detection reagent is a non-naturally occurring nucleic acid primer that acts as an initiation point of nucleotide extension along a complementary strand of a target polynucleotide. The SNP sequence information provided herein is also useful for designing primers, e.g., allele-specific primers, to amplify (e.g., using PCR) the SNP of the disclosed subject matter.

A SNP detection reagent may be an isolated or synthetic DNA or RNA polynucleotide probe or primer or PNA oligomer, or a combination of DNA, RNA and/or PNA that hybridizes to a segment of a target nucleic acid molecule containing one of the SNPs disclosed herein. A detection reagent in the form of a non-naturally occurring polynucleotide may optionally contain modified base analogs, intercalators, or minor groove binders. Multiple detection reagents such as probes may be, for example, affixed to a solid support (e.g., an array and bead) or supplied in solution (e.g., probe/primer sets for enzymatic reactions such as PCR, RT-PCR, TaqMan® assays, and primer-extension reactions) to form a SNP detection kit.

For analyzing SNPs, it can be appropriate to use oligonucleotides specific for alternative SNP alleles. Such oligonucleotides that detect single nucleotide variations in target sequences may be referred to by such terms as "allele-specific oligonucleotides," "allele-specific probes," or "allele-specific primers." The design and use of allele-specific probes for analyzing polymorphisms is described in, e.g., Mutation Detection: A Practical Approach, Cotton et al., eds., Oxford University Press (1998); Saiki et al., Nature 324:163-166 (1986); Dattagupta, EP235,726; and Saiki, WO 89/11548.

In another embodiment, a probe or primer may be designed to hybridize to a segment of target DNA such that the SNP aligns with either the 5'-most end or the 3'-most end of the probe or primer. When using an oligonucleotide ligation assay (U.S. Pat. No. 4,988,617), the 3' most nucleotide of the probe aligns with the SNP position in the target sequence.

Allele-specific probes are often used in pairs (or, less commonly, in sets of 3 or 4), and such pairs may be identical except for a one nucleotide mismatch that represents the allelic variants at the SNP position. Typically, one member of a probe pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity. Gibbs, Nucleic Acid Res 17:2427-2448 (1989). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456). This PCR-based assay can be utilized as part of the TaqMan® assay, described below.

A primer may contain a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In a preferred embodiment, the mismatched nucleotide in the primer is the second from the last nucleotide at the 3'-most position of the primer. In a more preferred embodiment, the mismatched nucleotide in the primer is the last nucleotide at the 3'-most position of the primer.

A SNP detection reagent may be labeled with a fluorogenic reporter dye that emits a detectable signal. While the preferred reporter dye is a fluorescent dye, any reporter dye that can be attached to a detection reagent such as an oligonucleotide probe or primer is suitable for use in the disclosed subject matter. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as TAMRA, especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., PCR Method Appl 4:357-362 (1995); Tyagi et al., Nature Biotechnology 14:303-308 (1996); Nazarenko et al., Nuc' Acids Res 25:2516-2521 (1997); U.S. Pat. Nos. 5,866,336 and 6,117,635.

Detection reagents may also contain other labels, including but not limited to, biotin for streptavidin binding, hapten for antibody binding, and an oligonucleotide for binding to another complementary oligonucleotide.

Reagents may not contain (or be complementary to) a SNP nucleotide as describe herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the Y-most end of the primer extension product, and in which the ddNTP is a nucleotide of a SNP disclosed herein, is a composition that is specifically herein). Thus, reagents that bind to a nucleic acid molecule in a region adjacent to a SNP site and that are used for assaying the SNP site, even though the bound sequences do not necessarily include the SNP site itself, are also contemplated by the disclosed subject matter.

For example, the SNP may be identified using single-base extension (SBE). SBE determines the identity of a nucleotide base at a specific position along a nucleic acid. In the method, an oligonucleotide primer hybridizes to a complementary region along the nucleic acid, to form a duplex, with the primer's terminal 3' end directly adjacent to the nucleotide base to be identified. The oligonucleotide primer is enzymatically extended by a single base in the presence of all four nucleotide terminators; the nucleotide terminator complementary to the base in the template being interrogated is incorporated and identified. The presence of all four terminators ensures that no further extension occurs beyond the single incorporated base. Many approaches can be taken for determining the identity of a terminator, including fluorescence labeling, mass labeling for mass spectrometry, measuring enzyme activity using a protein moiety, and isotope labeling.

Reagents and techniques described herein may be directed to performance of "Next Generation Sequencing." (See, e.g., Srivatsan et al., PLoS Genet 4: e100139 (2008); Rasmussen et al., Nature 463:757-762 (2010); Li et al., Nature 463: 311-317 (2010); Pelak et al., PLoS Genet 6: e1001111 (2010); Ram et al., Syst Biol Reprod Med (57(3):117-118 (2011); McEllistrem, Future Microbiol 4: 857-865 (2009); Lo et al., Clin Chem 55: 607-608 (2009); Robinson, Genome Biol 11:144 (2010); and Araya et al., Trends Biotechnology doi10. 1016.j.tibtech.2011.04.003 (2011)). For example, such techniques may involve the fragmentation of a genomic nucleic acid sample followed by parallel sequencing of those fragments and the alignment of the sequenced fragments to reconstruct the original sequence. Here, the genomic nucleic acid of interest is sheared into fragments and "adapters" (short nucleic acids of known sequence) are ligated to the fragments. Adaptor-modified fragments can be enriched via PCR. An adaptor-modified fragment (and amplified copies thereof, if present) may be flowed across a flow cell where the fragments are allowed to hybridize to primers immobilized on the surface of the cell. The fragments are then amplified by isothermal bridge amplification into a cluster consisting of thousands of molecules identical to the original. Sequencing primers can then be hybridized to the ends of one strand of the clusters, reversibly blocked, and labeled nucleotides added. The addition of each particular nucleotide can be identified by the label, then the label can be removed and the nucleotide un-blocked so that another blocked and labeled nucleotide can be added to identify the next position in the nucleic acid sequence. Once the desired number of rounds of addition, detection, and unblocking occur, the resulting sequences can be aligned.

It will be apparent to one of skill in the art that such primers and probes are directly useful as reagents for detecting the SNPs of the disclosed subject matter, and can be incorporated into any kit/system format.

SNP Genotyping Methods

SNP genotyping includes, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described herein. Examples of such applications include, but are not limited to, SNP-disease association analysis, disease predisposition screening, disease diagnosis, disease prognosis, disease progression monitoring, determining therapeutic strategies based on an individual's genotype ("pharmacogenomics"), developing therapeutic agents based on SNP genotypes associated with a disease or likelihood of responding to a drug, stratifying patient populations for clinical trials of a therapeutic, preventive, or diagnostic agent, and human identification applications such as forensics.

Nucleic acid samples can be genotyped to determine which allele is present at any given SNP position of interest by methods well known in the art. The neighboring sequence can be used to design SNP detection reagents such as oligonucleotide probes, which may optionally be implemented in a kit format. Exemplary SNP genotyping methods are described in Chen et al., "Single nucleotide polymorphism genotyping: biochemistry, protocol, cost and throughput," Pharmacogenomics J 3 (2):77-96 (2003); Kwok et al., "Detection of single nucleotide polymorphisms," Curr Issues Mol Biol 5 (2):43-60 (April 2003); Shi, "Technologies for individual genotyping: detection of genetic polymorphisms in drug targets and disease genes," Am J Pharmacogenomics 2 (3):197-205 (2002); and Kwok, "Methods for genotyping single nucleotide polymorphisms," Annu Rev Genom Hum Genet 2:235-58 (2001). Techniques for high-throughput SNP genotyping are described in Mamellos, "High-throughput SNP analysis for genetic association studies," Curr Opin Drug Disc Devel 6 (3):317-21 (May 2003).

SNP genotyping methods include, but are not limited to, TaqMan® assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, Oligonucleotide Ligation Assay (OLA: U.S. Pat. No. 4,988,167), multiplex ligation reaction sorted on genetic arrays, restriction-fragment length polymorphism, single base extension-tag assays, denaturing gradient gel electrophoresis, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

In one embodiment, SNP genotyping is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan® primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. These probes and primers can be readily incorporated into a kit format. The disclosed subject matter also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

Another method for genotyping the SNPs can be the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of Oligonucleotide Ligation Assay (OLA). The following U.S. patents describe OLA strategies for performing SNP detection: U.S. Pat. Nos. 6,027,889; 6,268,148; 5,494,810; 5,830,711 and 6,054,564. WO 97/31256 and WO 00/56927 describe OLA strategies for performing SNP detection using universal arrays, where a zipcode sequence can be introduced into one of the hybridization probes, and the resulting product, or amplified product, hybridized to a universal zip code array. U.S. application Ser. No. 01/17,329 (and Ser. No. 09/584,905) describes OLA (or LDR) followed by PCR, where zipcodes are incorporated into OLA probes, and amplified PCR products are determined by electrophoretic or universal zipcode array readout. U.S. applications 60/427,818, 60/445,636, and 60/445,494 describe SNPlex methods and software for multiplexed SNP detection using OLA followed by PCR, where zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

Typically, a mass spectrometry with primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions.

Primer extension assays may be used in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry," Rapid Comm. Mass Spect. 17 (11):1195-202 (2003).

SNPs can also be scored by direct DNA sequencing. A variety of automated sequencing procedures can be utilized (e.g., Biotechniques 19:448 (1995)), including sequencing by mass spectrometry. See, e.g., PCT International Publication No. WO 94/16101; Cohen et al., Adv Chromatogr 36:127-162 (1996); and Griffin et al, Appl Biochem Biotechnol 38:147-159 (1993). The nucleic acid sequences of the disclosed subject matter enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

Other methods that can be used to genotype the SNPs of the disclosed subject matter include single-strand conformational polymorphism (SSCP), and denaturing gradient gel electrophoresis (DGGE). Myers et al., Nature 313:495 (1985). SSCP identifies base differences by alteration in electrophoretic migration of single stranded PCR products, as described in Orita et al., Proc. Nat. Acad. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel. PCR Technology: Principles and Applications for DNA Amplification Chapter 7, Erlich, ed., W.H. Freeman and Co, N.Y. (1992).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

SNP Detection Kits and Systems

A person skilled in the art will recognize that, based on the SNP and associated sequence information disclosed herein, detection reagents can be developed and used to assay the SNP of the disclosed subject matter individually or in combination with other SNPs, and such detection reagents can be readily incorporated into one of the established kit or system formats which are well known in the art.

The terms "kits" and "systems," as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, and software recorded on a non-transitory processor-readable medium). Accordingly, the disclosed subject matter further provides SNP detection kits and systems, including but not limited to, packaged probe and primer sets (e.g., TaqMan® probe/primer sets), arrays/microarrays of nucleic acid molecules, and beads that contain one or more probes, primers, or other detection reagents for detecting one or more SNPs of the disclosed subject matter.

The kits/systems can optionally include various electronic hardware components; for example, arrays ("DNA chips") and microfluidic systems ("lab-on-a-chip" systems) provided by various manufacturers typically include hardware components. Other kits/systems (e.g., probe/primer sets) may not include electronic hardware components, but may include, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule.

A kit may further contain instructions for using the kit to detect the SNP-containing nucleic acid molecule of interest.

The instructions may include information which allows a user to identify whether an individual having or suspected of having an inflammation-related cardiovascular disorder/disease has genotype-specific differential expression of IL-1, i.e., is a "high" or "low" producer of IL-1, based upon the composite IL-1 genotype or IL-1 genotype patterns disclosed in Table 1 and Table 2 and has a relevant status of one or more clinical indicators, as disclosed herein. The instructions may include information which allows a user to decide on an appropriate drug or drugs (e.g., as disclosed in Table 3 to Table 7 and/or an alternate drug having a similar or identical mode of action as a drug disclosed in Table 3 to Table 7) and at an appropriate dose.

In one embodiment, kits are provided which contain the necessary reagents to carry out one or more assays to detect one or more SNPs disclosed herein. In another embodiment, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is the SNP of the disclosed subject matter. In some kits/systems, the allele-specific probes are immobilized to a substrate such as an array or bead.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A SNP detection kit/system can include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue or tumor specimens. Methods of preparing nucleic acids, proteins, and cell extracts are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700 sample preparation system, and Roche Molecular Systems' COBAS AmpliPrep System.

For genotyping SNPs, an exemplary microfluidic system may integrate, for example, nucleic acid amplification, primer extension, capillary electrophoresis, and a detection method such as laser induced fluorescence detection. In an exemplary process for using such an exemplary system, nucleic acid samples are amplified, preferably by PCR. Then, the amplification products are subjected to automated primer extension reactions using ddNTPs (specific fluorescence for each ddNTP) and the appropriate oligonucleotide primers to carry out primer extension reactions which hybridize just upstream of the targeted SNP. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

An exemplary kit allows a user to determine whether a subject has genotype-specific differential expression of IL-1, i.e., is a "high" or "low" producer of IL-1, based upon the composite IL-1 genotype or IL-1 genotype patterns disclosed in Table 1 and Table 2 and has a relevant status of one or more clinical indicators, as disclosed herein. The exemplary kit may include instructions having information which allows a user to decide on an appropriate drug or drugs (e.g., as disclosed in Table 3 to Table 7 and/or an alternate drug(s) having a similar or identical mode of action as a drug disclosed in Table 3 to Table 7) and at an appropriate dose.

Reports, Programmed Computers, and Systems

The results of a test provide an identification of a composite IL-1 genotype or IL-1 genotype pattern, as disclosed in Table 1 and Table 2 and identification of the status for one or more clinical indicators, as disclosed herein, which together determine an individual's predicted drug responsiveness (e.g., response of a drug or drugs disclosed in Table 3 to Table 7 and/or an alternate drug having a mode of action similar to or identical to a drug from Table 3 to Table 7). The results may be referred to herein as a "report". The report may include other information based on assaying the SNPs disclosed herein, alone or in combination with other SNPs, and/or an individual's allele/genotype at the SNPs disclosed herein, alone or in combination with other SNPs, etc.), and/or any other information pertaining to a test.

A tangible report can optionally be generated as part of a testing process (which may be interchangeably referred to herein as "reporting", or as "providing" a report, "producing" a report, or "generating" a report).

Examples of tangible reports may include, but are not limited to, reports in paper (such as computer-generated printouts of test results or hand written reports) or equivalent formats and reports stored on computer readable medium (such as a CD, USB flash drive or other removable storage device, computer hard drive, or computer network server, etc.). Reports, particularly those stored on computer readable medium, can be part of a database, which may optionally be accessible via the internet (such as a database of patient records or genetic information stored on a computer network server, which may be a "secure database" that has security features that limit access to the report, such as to allow only the patient and the patient's medical practitioners to view the report while preventing other unauthorized individuals from viewing the report, for example). In addition to, or as an alternative to, generating a tangible report, reports can also be displayed on a computer screen (or the display of another electronic device or instrument).

In addition to, or as an alternative to, the report may be "intangible" in that it is orally presented to another.

A tangible report may be hand written or may be prepared using a computer.

A report may be provided to the individual who can then implement the information and/or instructions contained therein.

A report may be provided to a health care professional who can then implement the information and/or instructions contained therein and/or instruct the individual (e.g., prescribe and make a recommendation).

A report can include, for example, an individual's predicted drug responsiveness (e.g., to a drug disclosed in Table 3 to Table 7 and/or an alternate drug having a mode of action similar to or identical to a drug from Table 3 to Table 7 based upon his/her composite IL-1 genotype or IL-1 genotype pattern, as disclosed in Table 1 and Table 2 and status of one or more clinical indicators, as disclosed herein; the allele/ genotype that an individual carries at the SNP locations disclosed herein; the status of his/her clinical indicators; and/or his/her composite IL-1 genotype or IL-1 genotype pattern. Thus, for example, the report can include information of medical/biological significance (e.g., drug responsiveness, suggested treatment, and prophylactic methods). The report may just include allele/genotype information and/or a composite IL-1 genotype or IL-1 genotype pattern and status of one or more clinical indicators but without including disease risk or other medical/biological significance; thus, the individual viewing the report can use the allele/genotype information and/or composite IL-1 genotype or IL-1 genotype pattern and status of one or more clinical indicators to determine the associated disease risk or other medical/biological significance from a source outside of the report itself, such as from a medical practitioner, publication, website, etc., which may optionally be linked to the report such as by a hyperlink.

A report can further be "transmitted" or "communicated" (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the internet, by facsimile, and/or by any wired or wireless communication methods known in the art) such as by being retrieved from a database stored on a computer network server.

Additional teaching relevant to the present invention are described in one or more of the following: U.S. Pat. Nos. 5,686,246, 5,698,399, 5,808,918, 6,108,635, 6,140,047, 6,210,877, 6,251,598, 6,268,142, 6,383,775, 6,437,216, 6,524,795, 6,551,785, 6,558,905, 6,706,478, 6,713,253, 6,720,141, 6,730,476, 6,733,967, 6,746,839, 7,723,028, 7,820,383, 8,101,360, 8,105,775, US 2002/0182612, US 2003/0100031, US 2003/0124524, US 2003/0152947, US 2003/0235890, US 2004/0152124, US 2005/0032077, US 2005/0064453, US 2005/0171338, US 2005/0282198, US 2006/0183161, US 2006/0252050, US 2007/0264645, US 2007/0275104, US 2008/0118920, US 2008/0187920, US 2008/0199865, US 2008/0254476, US 2008/0254477, US 2008/0254478, US 2008/0311581, US 2009/0023147, US 2009/0093396, US 2009/0163460, US 2009/0170105, US 2009/0191564, US 2010/0028893, US 2010/0129798, US 2010/0255475, US 2010/0279280, US 2011/0008906, US 2013/0011841, US 2003/0175764, US 2004/0110168, US 2010/0098775, US 2010/0098809, US 2010/0105038, US 2010/0112570, US 2010/0136561, US 2012/0208187, US 2013/0337448, and U.S. 62/277,760, each of which is incorporated herein by reference in their entireties.

Definitions

The term "single nucleotide polymorphisms" (SNPs) refers to a variation in the sequence of a gene in the genome of a population that arises as the result of a single base change, such as an insertion, deletion or, a change in a single base. A locus is the site at which divergence occurs. SNPs can result in modified amino acid sequences, altering structure and function of coded protein, and influence the splicing process when present at exon-intron transitions and modify gene transcription when part of promoters. This modification can lead to altered levels of protein expression.

As used herein the term subject is meant to include any human subject. A subject may be less than 60 years old. The subject may have had one, to, three or more cardiac events.

As used herein, the terms "treat," "treating," "treatment," and the like refer to reducing or ameliorating a disorder and/or a symptom associated therewith. It will be appreciated that, although not precluded, treating a disorder or condition does not require that the disorder, condition or symptoms associated therewith be completely eliminated. Treating may include a health care professional or diagnostic scientist making a recommendation to a subject for a desired course of action or treatment regimen, e.g., a prescription.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the terms "drug", "medication", "therapeutic", "active agent", "therapeutic compound", "composition", or "compound" are used interchangeably and refer to any chemical entity, pharmaceutical, drug, biological, botanical, and the like that can be used to treat or prevent a disease, illness, condition, or disorder of bodily function. A drug may comprise both known and potentially therapeutic compounds. A drug may be determined to be therapeutic by screening using the screening known to those having ordinary skill in the art. A "known therapeutic compound", "drug", or "medication" refers to a therapeutic compound that has been shown (e.g., through animal trials or prior experience with administration to humans) to be effective in such treatment. A "therapeutic regimen" relates to a treatment comprising a "drug", "medication", "therapeutic", "active agent", "therapeutic compound", "composition", or "compound" as disclosed herein and/or a treatment comprising behavioral modification by the subject and/or a treatment comprising a surgical means.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "one or more", "at least one", "more than one", and the like are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting.

Unless otherwise defined, all technical and scientific terms used herein have the same meaning as commonly understood by one of ordinary skill in the art to which this application belongs and as commonly used in the art to which this application belongs; such art is incorporated by reference in its entirety.

Any of the above aspects and embodiments can be combined with any other aspect or embodiment as disclosed in the Summary, Drawings, and/or in the Detailed Description sections, including the below examples/embodiments.

Example 1 General Methods

Study Population

This study enrolled 603 consecutive patients undergoing a diagnostic coronary angiography based on clinical suspicion of coronary artery disease at the $2^{nd}$ Department of Cardiology in the University Hospital of Ioannina and the Catheterization Laboratory of 1st IKA Hospital in Athens, from January 2010 to December 2012. Patients were between 18 years to 90 years at entry (index coronary angiography) and of both genders. Patients with a history of any coronary revascularization procedure, severe valvular disease, congenital heart disease, cardiomyopathies as well as those on hemodialysis were excluded. Additionally, patients with diabetes mellitus were excluded to be able to compare to prior studies[1,2] where such patients were excluded, since they are very high risk group that may mask other underlying relationships.

Study Design

The study was prospectively designed to test the association of CAD with pro-inflammatory and pro-thrombotic biomarkers in relation to the presence of specific IL-1 genotype groups known to be associated with higher inflammatory responses. The study protocol was approved by the Ethics Committee at University Hospital of Ioannina. The study complied with the Declaration of Helsinki and all participants provided written informed consent.

Parameters recorded in the study were derived from patient's medical history, physical examination, laboratory evaluations, and coronary angiography. All subjects underwent catheterization and coronary angiography according to the standard Judkins technique. Angiograms were assessed in multiple projections independently by two experienced operators and a consensus was reached. Angiographically significant disease was defined as diameter stenosis>50% in any one major epicardial coronary artery.

Blood samples were drawn after an overnight fast and just before coronary angiography for stable coronary syndromes. In patients with unstable coronary syndromes blood samples for determination of lipids levels and fasting glucose were drawn either before coronary angiography or the next morning depending on the presence of fasting state.

Of the 603 patients enrolled, 512 patients (85%) were contacted by a follow-up by telephone between May and July 2015 [median follow-up of 45 months (interquartile range, 24-60 months)]. The remaining 91 patients either refused to participate in the follow-up or could not be contacted. Of the 512 patients with available follow-up, 52 (10%) had one or more events categorized as cardiovascular death, acute coronary syndrome, new revascularization unrelated to the original angiography, stroke, or death of any cause. The follow-up events of these patients consisted of 22 deaths (17 cardiac), 16 myocardial infarctions, 8 coronary revascularizations, and 20 strokes.

Genetic Analysis

Single nucleotide polymorphisms (SNPs) were genotyped at two loci in the IL-1β gene (rs16944 and rs1143634) and one in the IL-1α gene (rs17561), as previously described.[1,2] Briefly, extracted DNA from the participants was sent to Interleukin Genetics, Inc. (Waltham, Mass.), and genotyped at their CLIA certified genotyping laboratory. Multiplexed polymerase chain reactions (PCR) specifically targeting surrounding sequences for each of the SNPs were treated with exonuclease I and shrimp alkaline phosphatase (USB). Primer extension reactions and genotype detection was performed using an automated genotyping system [Genome Lab SNPStream (Beckman-Coulter)]. Allele calls were determined by the SNPstream software and verified by a laboratory technologist.

IL-1 Composite Genotype Patterns

IL-1 composite genotype patterns (Positive-IL1(+) and Negative (IL1(−)) are identical to those used in Tsimikas, et al.[2] and include the single nucleotide polymorphisms: rs 17561 (G>T), rs1143634 (C>T), and rs16944 (C>T).

Biomarker Analysis

Total cholesterol, HDL cholesterol (HDL-C) and triglycerides were measured with commercially available kits. LDL cholesterol (LDL-C) was estimated using the Friedewald formula. Serum hsCRP was measured using rate turbidimetry (IMMAGE Immunochemistry Systems and Calibrator 5 Plus, Beckman Coulter Inc, Fullerton, Calif., USA).

OxPL-apoB levels were measured in a chemiluminescent immunoassay using the murine monoclonal antibody E06 that recognizes the phosphocholine group on oxidized but not on native phospholipids (details in Byun et al and references therein) and results reported in nanomoles/liter (nM). The OxPL-apoB measure reflects OxPL on all apoB-100-containing lipoproteins, but we have shown previously that it primarily reflects the biological activity and clinical risk of Lp(a), which is the major lipoprotein carrier of OxPL in plasma, and which carries ~85% of OxPL on apoB-100 containing lipoproteins. Lp(a) levels were determined with a sandwich ELISA as previously described.[4]

Statistical Analysis

For genetic data analysis, standard data quality checks including genotype call rate, percentage of missing genotypes, minor allele frequencies, and tests of HWE were carried out.

Logistic regression was used to determine odds ratios (OR) for CAD of each quartile of OxPL-apoB and Lp(a) relative to the lowest quartile. Trend tests were done by repeating analyses with quartiles coded numerically. Analyses were done for all patients and with stratification for IL-1 genotype and age≤60.

Multivariate logistic analysis was used to adjust for factors known to modify risk for CAD including sex, current smoking, hypertension, triglycerides (per doubling), LDL cholesterol (per increase of 25 mg/dl), HDL cholesterol (per increase of 25 mg/dl) and experimental factors of hsCRP (per doubling), OxPL/apoB (per doubling), Lp(a) (per doubling), and presence of IL-1+ genotype. Formal testing for statistical interaction of IL-1 genotype with OXPL/apoB and lp(a) on CAD risk was carried out by adding an interaction term to the logistic regression model. Event-free survival curves were constructed by the Cox regression proportional hazard regression method. Multivariable analysis was used to adjust for gender, current smoking, hypertension, triglycerides (per doubling), LDL cholesterol (per increase of 25 mg/dl), HDL cholesterol (per increase of 25 mg/dl) and hsCRP (per doubling). Events were defined as CVD death, non-fatal MI, new revascularization and stroke/TIA subsequent to enrollment during the follow-up period.

Example 2: Baseline Characteristics of the Study Group

The baseline characteristics of the 603 patients, separated by IL1 status, are presented in Table 8. The total cohort had a mean age of 63±11 and was 71% male. 390 patients (65%) were IL-1(+), typical of prior data in Caucasian populations. Cardiovascular risk factors were prevalent and included current smoking (41%), hypertension (73%), hypercholesterolemia (78%), and family history of CAD (33%). The baseline use of anti-platelet agents and statins was 31% and 42%, respectively. The indication for angiography was acute coronary syndrome in 19% and suspected CAD in 81% of patients. Mean LDL-C was 126±40 mg/dL, median (IQR) Lp(a) was 9.2 (4.4, 20.9) mg/dl and median (IQR) OxPL-apoB was 12.5 (8.1, 14.0). The baseline characteristics were not significantly different between IL1(+) and IL1(−) groups, except for family history, total cholesterol and LDL-C being higher in the IL1(−) group. Also, the baseline characteristics were similar between patients with and without follow-up data.

Figure 5:
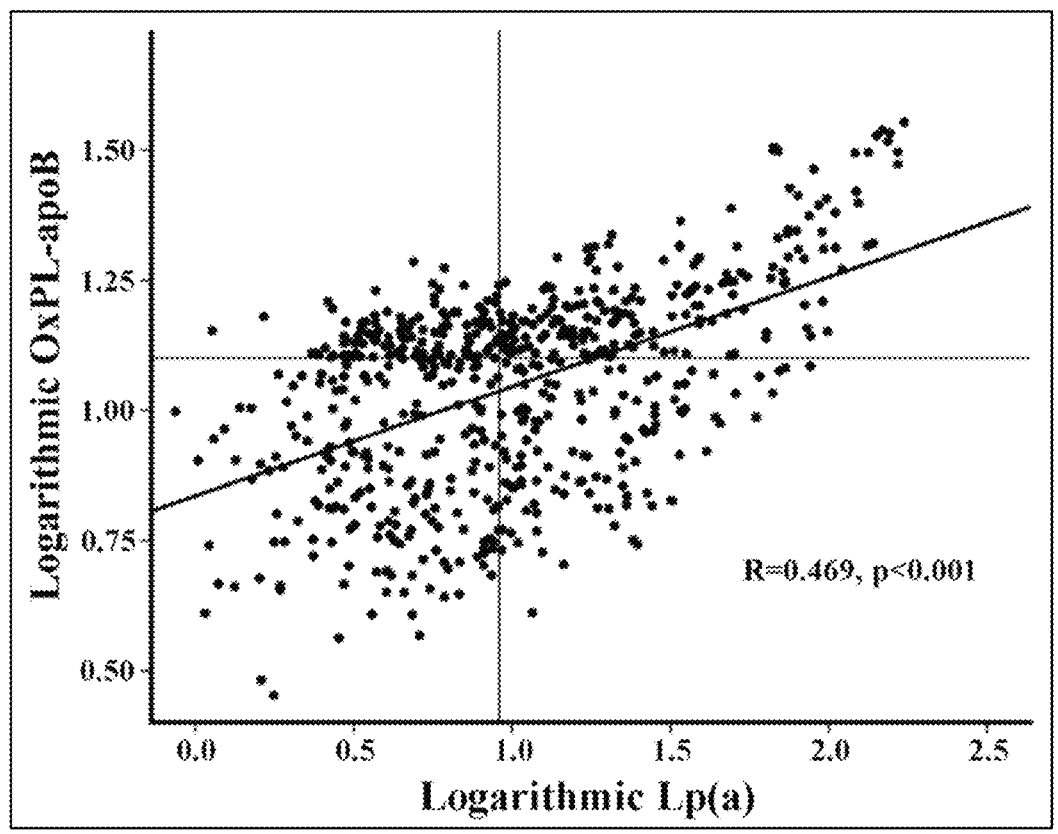
FIG. 5 is a plot showing Spearman correlations of logarithmic modified Lp(a) and OxPL-apoB levels.

The Spearman correlation of Lp(a) levels to OxPL-apoB levels in the entire group was R=0.469, p<0.001 (FIG. 5), and R=0.467, p<0.001 in IL1(+) and R=0.473, p<0.001 in IL1(−) patients. Lp(a) and OxPL-apoB were significantly but weakly correlated only with the presence of a family history of CAD (R=0.086, p=0.034 and R=0.135, p=0.001 respectively).

Example 3: Relationship of Lp(a) and OxPL-apoB and for Angiographically-Determined CAD The number (%) of patients with no CAD was 265 (44%), and non-significant CAD was 51 (9%). Among the 287 (47%) with CAD, the distribution of 1-vessel, 2-vessels and 3-vessels were as follows: 316 (53%), 183 (30%), 84 (14%) and 20 (3%), respectively.

Analysis by Lp(a) quartiles revealed a linear, significant relationship between increasing levels of Lp(a) and OR for angiographically determined CAD in IL1(+) patients≤60 years old, reaching an OR (95% CI) of 2.90 (1.07-7.86) (p=0.036) for quartile 4 versus quartile 1 (Table 9). In contrast, no significant differences were noted in IL1(−) patients or in patients>60 years old.

Analysis by OxPL-apoB quartiles revealed similar trends, but with borderline non-significance, for angiographically determined CAD in IL1(+) patients≤60 years of age, reaching an OR (95% CI) of 2.29 (0.72-7.31) (p=0.056 for quartile 4 versus quartile 1 (Table 10).

Figure 6:
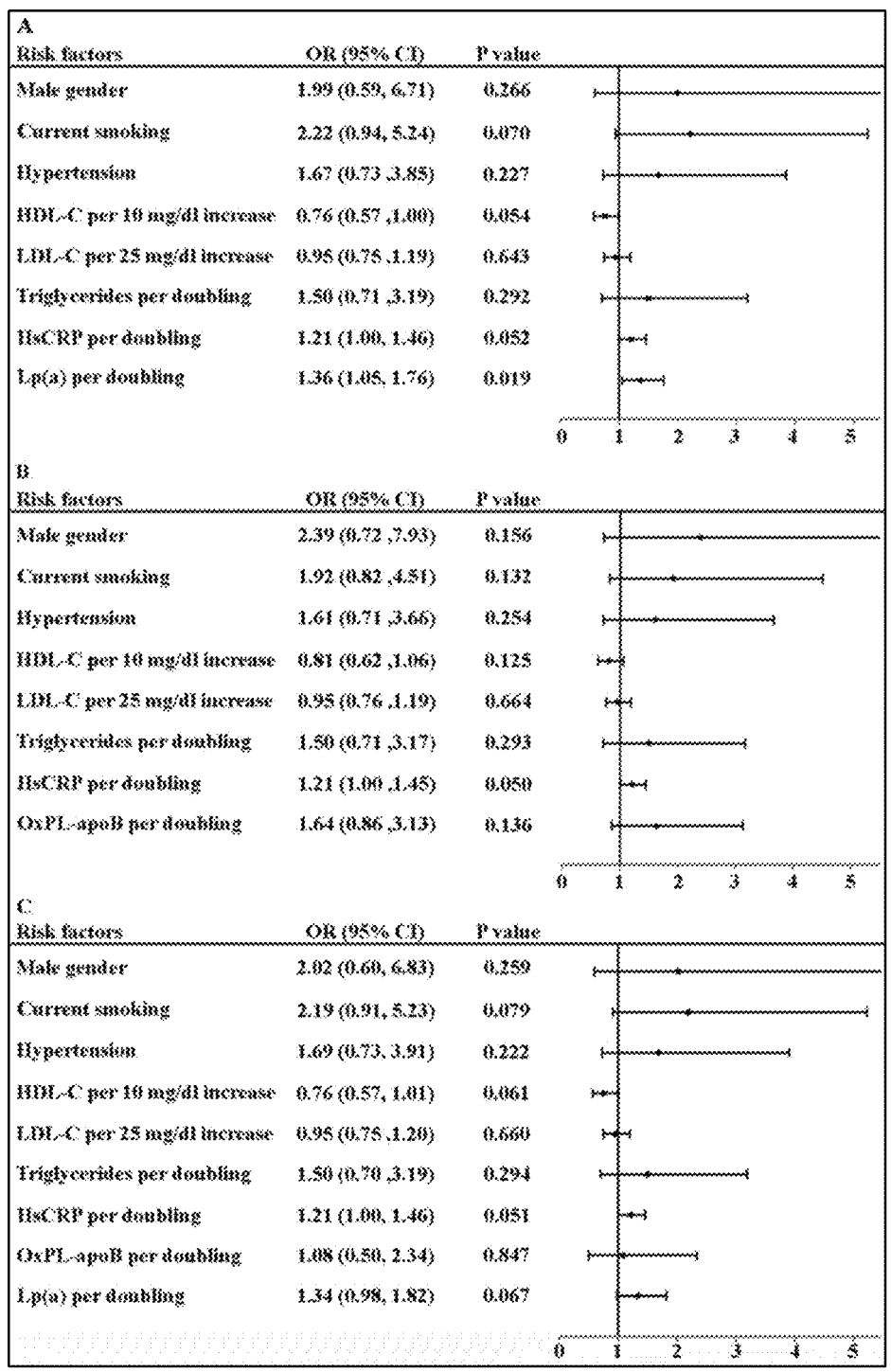
FIG. 6 is a series of graphs and their associated statistics showing multivariable analysis derived odds ratios for CAD associated with Lp(a), OxPL-apoB, or both among the traditional risk factors. Panel A, top, shows multivariable analysis derived odds ratios for CAD associated with Lp(a) among the traditional risk factors. CI=confidence interval, LDL-C=low-density lipoprotein (per increase of 25 mg/dl), hsCRP=high sensitivity C-reactive protein (per doubling), OxPL-apoB (per doubling), Lp(a) (per doubling), HDL-C=high-density lipoprotein (per increase of 10 mg/dl), and triglycerides (per doubling). Panel B, middle, shows multivariable analysis derived odds ratios for CAD associated with OxPL-apoB among the traditional risk factors. CI=confidence interval, LDL-C=low-density lipoprotein (per increase of 25 mg/dl), hsCRP=high sensitivity C-reactive protein (per doubling), OxPL-apoB (per doubling), Lp(a) (per doubling), HDL-C=high-density lipoprotein (per increase of 10 mg/dl), and triglycerides (per doubling). Panel C, bottom shows multivariable analysis derived odds ratios for CAD associated with both Lp(a) and OxPL-apoB among the traditional risk factors. CI=confidence interval, LDL-C=low-density lipoprotein (per increase of 25 mg/dl), hsCRP=high sensitivity C-reactive protein (per doubling), OxPL-apoB (per doubling), Lp(a) (per doubling), HDL-C=high-density lipoprotein (per increase of 10 mg/dl), and triglycerides (per doubling).

In patients≤60 years old, a multivariable-adjusted logistic regression analysis was performed assessing angiographically-determined CAD, which included sex, current smoking, hypertension, HDL-C per 10 mg/dL increase, LDL-C per 25 mg/dL increase, triglycerides per doubling, hsCRP per doubling and Lp(a) per doubling. In this model, a doubling of Lp(a) was the only significant predictor of CAD with an OR (95% CI) of 1.36 (1.05-1.76), p=0.019 (FIG. 6A). Performing a similar multivariable analysis but substituting a doubling of OxPL-apoB for Lp(a) showed an OR (95% CI) of 1.64 (0.86-3.13), p=0.136 (FIG. 6B).

Example 4: Event-Free Survival During Median 45 Month Follow Up

Hazard ratios were determined with multivariable-adjusted Cox proportional hazard analysis by evaluating above or below the median (9.2 mg/dL) Lp(a) according to IL1 genotype status (4 groups: IL1(+) patients with above median Lp(a), IL1(+) patients with below median Lp(a), IL1(−) patients with above median Lp(a) and IL1(−) patients with below median Lp(a)). Co-variates included age, gender, active smoking, hypertension, HDL-C, LDL-C, triglycerides and hsCRP. There were 46 MACE events, defined as CVD death, non-fatal MI, stroke and revascularization. Significant differences in time to MACE were present among the 4 groups, with the worse event-free cumulative survival present in the IL1(+) subjects with above median Lp(a), with a HR (95% CI) of 3.59 (1.07-12.03) (p=0.039) compared to IL1(−) subjects with below median Lp(a).

Figure 7:
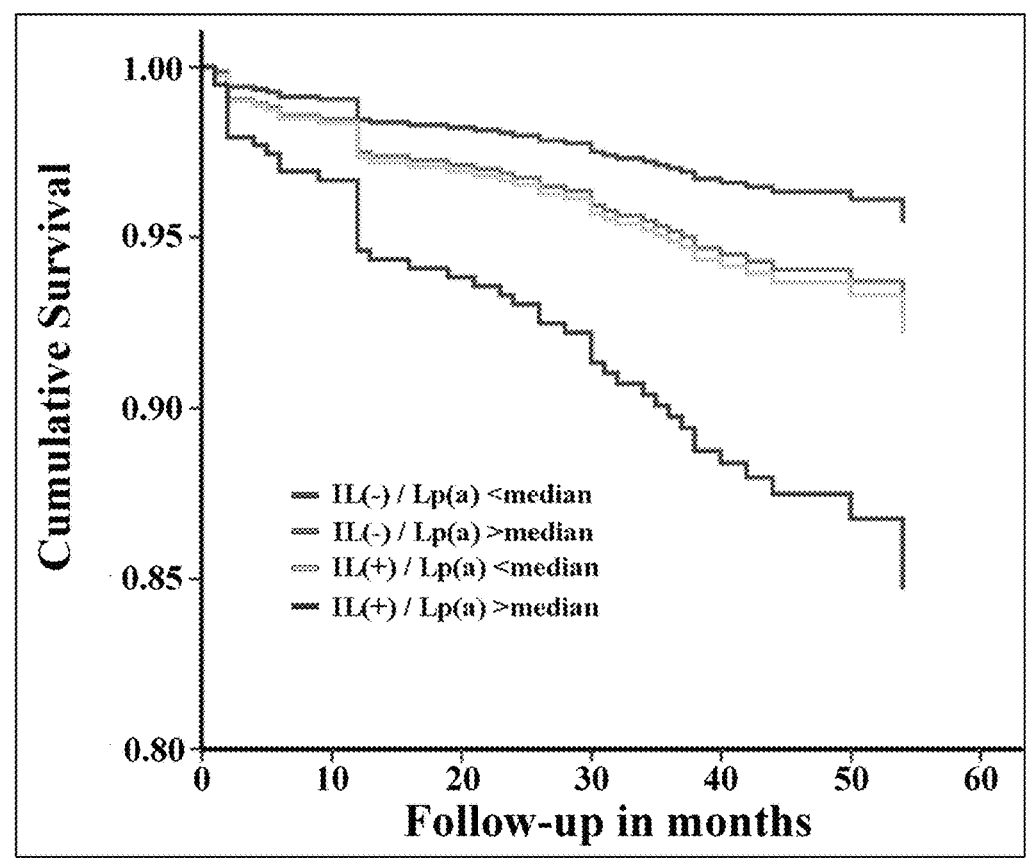
FIG. 7 is a plot showing cumulative event-free survival period over a median of 43 months for clinical outcomes of CVD death, non-fatal MI, and stroke/TIA plotted according to medians of Lp(a) and IL-1 genotype by Cox proportional hazard method.

Additional analysis comparing IL1(+) subjects with above median Lp(a) against the other 3 groups showed a HR (95% CI) of 2.29 (1.27, 4.13), p=0.006 (FIG. 7). Removing the 8 cases of revascularization from the MACE endpoint increased the HR (95% CI) for in the IL1(+) subjects with above median Lp(a) versus IL1(−) subjects with below median Lp(a) to 10.86 (1.46-81.05) (p=0.020). The OR (95% CI) was 3.10 (1.61, 5.97), p=0.001 versus the other 3 groups. Adding OxPL-apoB to the multivariable model resulted in persistence of significance for IL1(+) patients with above median Lp(a), with a HR OR (95% CI) at 3.78 (1.10-13.01) (p=0.035) compared to IL1(−) subjects with below median Lp(a) Similar results were present for the other analyses as above when adding OxPL-apoB to the models (data not shown). Interactions of quartiles of Lp(a) with IL1 genotype status were significant in patients≤60 years old (p=0.046).

Evaluating OxPL-apoB in the multivariable model without Lp(a) showed an OR (95% CI) for Q4 vs Q1 of 2.42 (0.71-8.28) (p=0.160).

Example 5: Relationship of Lp(A), IL1 Genotypes and hsCRP hsCRP levels did not differ significantly between IL1(+) and IL1(−) patients. Lp(a) was positively yet weakly correlated with hsCRP (R=0.096, p=0.020). In the overall group, hsCRP was an independent predictor of CAD in both IL1(+) (OR (95% CI) of 1.19, P=0.003) and IL1(−) (OR of 1.54, P<0.001) patients; a similar effect was shown in IL1(+) patients≤60 years old. The OR (95% CI) for the Lp(a) association with CAD in IL1(+) patients with hsCRP>2.82 mg/L (median value) was 2.80, p=0.038 for quartile IV vs quartile I, and in those with hsCRP<2.82 mg/L, the OR was 1.59, p=0.289 for quartile IV vs quartile I. Removing the 69 patients with recent acute coronary syndrome yielded similar results, with OR (95% CI) of 3.02, p=0.046 for the Lp(a) association with CAD in IL1(+) patients with hsCRP above the median (quartile IV vs quartile I), and OR (95% CI) 1.34, p=0.544 in those below the median.

TABLE 1

Baseline characteristics in the entire population and by IL-1 genotype status

|  | All patients (n = 603) | IL-1(+) patients (n = 390) | IL-1(−) patients (n = 213) | P value (IL1(+) vs IL1(−)) |
|---|---|---|---|---|
| Age, years | 63 ± 11 | 64 ± 11 | 62 ± 10 | 0.079 |
| Males, n (%) | 430 (71) | 275 (71) | 155 (73) | 0.573 |
| Current Smokers, n (%) | 249 (41) | 164 (42) | 85 (40) | 0.665 |
| Hypertension, n (%) | 438 (73) | 286 (73) | 152 (71) | 0.633 |
| Hypercholesterolemia, n (%) | 473 (78) | 303 (78) | 170 (80) | 0.605 |
| Family history of CAD, n (%) | 198 (33) | 116 (30) | 82 (39) | 0.030 |
| Medications, n (%) |  |  |  |  |
| Antiplatelet agents | 185 (31) | 123 (32) | 62 (29) | 0.580 |
| Statins | 252 (42) | 169 (43) | 83 (39) | 0.342 |
| Beta blockers | 180 (30) | 115 (30) | 65 (31) | 0.852 |
| RAAS inhibitors | 215 (36) | 133 (34) | 82 (39) | 0.287 |
| Calcium channel blockers | 157 (26) | 109 (28) | 48 (23) | 0.174 |
| Diuretics | 134 (22) | 92 (24) | 42 (20) | 0.306 |
| History of CAD, n (%) | 106 (18) | 64 (16) | 42 (20) | 0.315 |
| Indication for angiography |  |  |  |  |
| Acute coronary syndrome | 114 (19) | 69 (18) | 45 (21) | 0.317 |
| Suspected stable CAD | 489 (81) | 321 (82) | 168 (79) | 0.765 |
| Systolic BP, mmHg | 134 ± 21 | 133 ± 21 | 135 ± 19 | 0.206 |
| Diastolic BP, mmHg | 79 ± 12 | 79 ± 13 | 80 ± 12 | 0.476 |
| Body mass index, kg/m$^2$ | 27.8 ± 3.7 | 27.8 ± 3.8 | 28.0 ± 3.6 | 0.556 |
| Fasting glucose, mg/dl | 99 (91, 109) | 99 (91, 108) | 99 (91, 110) | 0.733 |
| MDRD-GFR, ml/min/1.73 m$^2$ | 73.91 ± 16.5 | 73.2 ± 17.0 | 75.2 ± 15.6 | 0.160 |
| Total cholesterol, mg/dl | 195 ± 43 | 192 ± 43 | 199 ± 43 | 0.047 |
| HDL cholesterol, mg/dl | 43 ± 16 | 42 ± 16 | 43 ± 17 | 0.765 |
| LDL cholesterol, mg/dl | 126 ± 40 | 123 ± 40 | 130 ± 40 | 0.035 |
| Triglycerides, mg/dl | 117 (92, 164) | 118 (92, 169) | 112 (91, 156) | 0.570 |
| Hs-CRP, mg/L | 2.8 (1.16, 6.9) | 2.7 (1.1, 6.8) | 3.2 (1.0, 7.5) | 0.477 |
| Lp(a), mg/dl | 9.2 (4.4, 20.9) | 8.8 (4.3, 20.4) | 10.2 (4.6, 21.5) | 0.428 |
| OxPL-apoB, nM | 12.5 (8.1, 14.0) | 12.5 (8.29, 14.7) | 12.6 (7.8, 14.9) | 0.942 |
| Presence of CAD, n (%) |  |  |  |  |
| No CAD | 265 (44) | 172 (44) | 93 (44) | 0.974 |
| Non-significant CAD (<50% stenosis) | 51 (9) | 33 (9) | 18 (8) | 0.965 |
| Any | 287 (47) | 185 (47) | 102 (48) | 0.848 |

TABLE 1-continued

Baseline characteristics in the entire population and by IL-1 genotype status

|  | All patients (n = 603) | IL-1(+) patients (n = 390) | IL-1(−) patients (n = 213) | P value (IL1(+) vs IL1(−)) |
|---|---|---|---|---|
| 1-vessel | 183 (30) | 115 (30) | 68 (32) | 0.540 |
| 2-vessel | 84 (14) | 59 (15) | 25 (12) | 0.314 |
| 3-vessel | 20 (3) | 11 (3) | 9 (4) | 0.348 |

Abbreviations: IL-1, interleukin1; CAD, coronary artery disease; BP, blood pressure; MDRD-GFR, Modification of Diet in Renal Disease study - Glomerular filtration rate; HDL, high density lipoprotein; LDL, Low density lipoprotein; hsCRP, high sensitivity C-reactive protein; Lp(a), lipoprotein a; OxPL-apoB, oxidized phospholipids on apolipoprotein B.

TABLE 2

Odds ratios for angiographically-determined CAD (>50% diameter stenosis) in patients ≤60 and >60years old according to quartiles for Lp(a), and IL-1 genotype.

| | IL-1(+) | | | IL-1(−) | | |
|---|---|---|---|---|---|---|
| Age ≤60 yr | Total No. | No. with CAD (%) | OR (95% CI) | Total No. | No. with CAD (%) | OR (95% CI) |
| Quartile I | 40 | 9 (23) | 1.00 | 26 | 11 (42) | 1.00 |
| Quartile II | 35 | 12 (34) | 1.78 (0.65-4.98) | 17 | 10 (59) | 1.95 (0.56-6.73) |
| Quartile III | 29 | 11 (38) | 2.11 (0.73-6.05) | 25 | 10 (40) | 0.91 (0.30-2.78) |
| Quartile IV | 35 | 16 (46) | 2.90 (1.07-7.86) | 28 | 15 (54) | 1.57 (0.54-4.61) |
| OR (95% CI) per quartile | | | 1.39 (1.02-1.90) | | | 1.08 (0.77-1.53) |
| P for trend | | | 0.036 | | | 0.644 |

| | IL-1(+) | | | IL-1(−) | | |
|---|---|---|---|---|---|---|
| Age >60 yr | Total No. | No. with CAD (%) | OR (95% CI) | Total No. | No. with CAD (%) | OR (95% CI) |
| Quartile I | 58 | 30 (52) | 1.00 | 26 | 10 (39) | 1.00 |
| Quartile II | 68 | 36 (53) | 1.05 (0.52-2.12) | 31 | 14 (45) | 1.32 (0.46-3.81) |
| Quartile III | 66 | 35 (53) | 1.05 (0.52-2.14) | 31 | 14 (45) | 1.32 (0.46-3.81) |
| Quartile IV | 59 | 36 (61) | 1.46 (0.70-3.04) | 29 | 18 (62) | 2.62 (0.88-7.78) |
| OR (95% CI) for quartile | | | 1.21 (0.95-1.53) | | | 1.33 (0.95-1.87) |
| P for trend | | | 0.130 | | | 0.097 |

Abbreviations: CAD, coronary artery disease; Lp(a), lipoprotein(a); IL-1, interleukin 1; OR, odds ratio. Quartile I Lp(a) <4.40 mg/dL, Quartile II Lp(a) 4.40-9.10 mg/dL, Quartile III Lp(a) 9.15-20.9 mg/dL and Quartile IV Lp(a) >20.9 mg/dL.

TABLE 3

Odds ratios for angiographically-determined CAD (>50% diameter stenosis) in patients ≤60 and ≥60 years old according to quartiles for OxPL-apoB and IL-1 genotype.

| | IL-1(+) | | | IL-1(−) | | |
|---|---|---|---|---|---|---|
| Age ≤60 yr | Total No. | No. with CAD (%) | OR (95% CI) | Total No. | No. with CAD (%) | OR 95% CI) |
| Quartile I | 25 | 6 (24) | 1.00 | 31 | 18 (58) | 1.00 |
| Quartile II | 45 | 12 (45) | 1.15 (0.37-3.57) | 22 | 10 (46) | 0.60 (0.20-1.81) |
| Quartile III | 38 | 17 (45) | 2.56 (0.84-7.85) | 18 | 8 (44) | 0.58 (0.18-1.87) |
| Quartile IV | 31 | 13 (42) | 2.29 (0.72-7.31) | 25 | 10 (40) | 0.48 (0.17-1.41) |
| OR (95% CI) per quartile | | | 1.41 (0.99-2.00) | | | 0.79 (0.56-1.12) |
| P for trend | | | 0.056 | | | 0.185 |

| | IL-1(+) | | | IL-1(−) | | |
|---|---|---|---|---|---|---|
| Age >60 yr | Total No. | No. with CAD (%) | OR (95% CI) | Total No. | No. with CAD (%) | OR (95% CI) |
| Quartile I | 65 | 39 (60) | 1.00 | 26 | 15 (58) | 1.00 |
| Quartile II | 59 | 30 (51) | 0.69 (0.34-1.41) | 27 | 12 (44) | 0.59 (0.20-1.74) |
| Quartile III | 59 | 31 (53) | 0.74 (0.36-1.51) | 28 | 11 (39) | 0.48 (0.16-1.41) |
| Quartile IV | 58 | 37 (54) | 0.80 (0.40-1.58) | 36 | 18 (50) | 0.73 (0.27-2.03) |

TABLE 3-continued

Odds ratios for angiographically-determined CAD (>50% diameter stenosis) in patients ≤60 and ≥60 years old according to quartiles for OxPL-apoB and IL-1 genotype.

| OR (95% CI) per quartile | 0.94 (0.76-1.17) | 0.91 (0.66-1.26) |
|---|---|---|
| P for trend | 0.583 | 0.578 |

Abbreviations: CAD, coronary artery disease; OxPL/apoB, oxidized phospholipids on apolipoprotein B; IL-1, interleukin 1; OR, odds ratio. Quartile I OxPL-apoB <8.0 nmol/L, Quartile II OxPL-apoB 8.0-12.5 nmol/L, Quartile III OxPL-apoB 12.51-14.7 nmol/L and Quartile IV OxPL-apoB >14.7 nmol/L.

REFERENCES

Chen, H., et al., "Single Nucleotide Polymorphisms in the Human Interleukin-1B Gene Affect Transcription According to Haplotype Context." *Human Molecular Genetics* (2006), 15.4: 519-529.

Libby, P., "History of Discovery: Inflammation in Atherosclerosis." *Arterioscler Thromb Vasc Biol.* (2012) 32(9): 2045-2015.

Ray, K K., "Interleukin-1 Revisited: Further Insights Into Its Role in Atherosclerosis and as a Potential Therapeutic Target for Treatment." *Journal of the American College of Cardiology* (2014), 63.17: 1735-1738

Ridker, P. M. "Targeting inflammatory pathways for the treatment of cardiovascular disease." *European Heart Journal* (2014) 35.

Rogus J., et al., "IL1B Gene Promoter Haplotype Pairs Predict Clinical Levels of Interleukin-1β and C-reactive Protein." *Human Genetics* (2008). 123.4: 387-398.

Ross, "Atherosclerosis—An inflammatory disease." *N Engl J Med* (1999); 340:115-126.

Tsimikas S., et al., "Antisense oligonucleotides targeting apolipoprotein(a) in people with raised lipoprotein(a): two randomized, double-blind, placebo controlled, dose-ranging trials." *The Lancet*, Sep. 21, 2016.

Tsimikas S., et al., "Oxidized Phospholipids, Lp(a) Lipoprotein, and Coronary Artery Disease." *New England Journal of Medicine* (2005), 353:46-57.

Tsmikas S., et al., "Pro-Inflammatory Interleukin-1 Genotypes Potentiate the risk of Coronary Artery Disease and Cardiovascular Events Mediated by Oxidized Phospholipids and Lipoprotein(a)." *J. Am. College of Cardiology* (2014). Vol. 63, No. 17.

Yusuf et al., "Effect of potentially modifiable risk factors associated with myocardial infarction in 52 countries (the INTERHEART study): case-control study." *Lancet,* 364: 937-52 (2004).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject at risk of a future cardiac event comprising:
(a) obtaining information regarding the human subject's single nucleotide polymorphism (SNP) alleles for each of the rs16944 polymorphic locus, the rs1143623 polymorphic locus, the rs4848306 polymorphic locus, the rs17561 polymorphic locus, and the rs1143634 polymorphic locus;
(b) determining that the subject has a positive IL-1 genotype pattern when the IL-1 genotype pattern obtained in (a) matches an IL-1 genotype pattern that is selected from the group consisting of:
(i) T/T or T/G at rs17561, C/C, T/T, C/T or T/C at rs4848306, G/G at rs1143623, C/C at rs16944 and T/T or T/C at rs1143634;
(ii) G/G at rs17561, C/C, T/T, C/T or T/C at rs4848306, G/G at rs1143623, C/C at rs16944 and C/C, T/T, C/T or T/C at rs1143634;
(iii) G/G, T/T, G/T or T/G at rs17561, C/C, T/T, C/T or T/C at rs4848306, G/G at rs1143623, C/C at rs16944 and C/C at rs1143634;
(iv) T/T or T/G at rs17561, C/C or C/T at rs4848306, G/G at rs1143623, C/T at rs16944 and T/T or T/C at rs1143634;
(v) G/G at rs17561, C/C or C/T at rs4848306, G/G at rs1143623, C/T at rs16944 and C/C, T/T, C/T or T/C at rs1143634;
(vi) G/G, T/T, G/T or T/G at rs17561, C/C or C/T at rs4848306, G/G at rs1143623, C/T at rs16944 and C/C at rs1143634;
(vii) T/T or T/G at rs17561, C/C at rs4848306, C/G at rs1143623, C/T at rs16944 and T/T or T/C at rs1143634; 2
(viii) G/G at rs17561, C/C at rs4848306, C/G at rs1143623, C/T at rs16944 and C/C, T/T, C/T or T/C at rs1143634;
(ix) G/G, T/T, G/T or T/G at rs17561, C/C at rs4848306, C/G at rs1143623, C/T at rs16944 and C/C at rs1143634;
(x) T/T or T/G at rs17561, C/C at rs4848306, G/G at rs1143623, T/T at rs16944 and T/T or T/C at rs1143634;
(xi) G/G at rs17561, C/C at rs4848306, G/G at rs1143623, T/T at rs16944 and C/C, T/T, C/T or T/C at rs1143634; and
(xii) G/G, T/T, G/T or T/G at rs17561, C/C at rs4848306, G/G at rs1143623, T/T at rs16944 and C/C at rs1143634;
(c) determining at least one of:
(i) a plasma concentration of LDL-C; and/or
(ii) a plasma concentration of Lp(a)
in a sample obtained from the subject;
(d) diagnosing the subject as at risk of a cardiac event when the subject has a positive IL-1 pattern determined in step (b) and
(i) a total LDL-C plasma concentration of at least 50 mg/dL, and/or
(ii) a total Lp(a) plasma concentration of at least 5 mg/dL; and
(e) administering canakinumab to the diagnosed subject, thereby reducing the probability of a cardiac event in the subject.

2. The method of claim 1, further comprising administering one or more of Evolocumab, Alirocumab, APO(a)-$L_{RX}$ and ARC-LPA.

\* \* \* \* \*

UNITED STATES PATENT AND TRADEMARK OFFICE
CERTIFICATE OF CORRECTION

PATENT NO.         : 10,337,070 B2
APPLICATION NO.    : 15/649175
DATED              : July 2, 2019
INVENTOR(S)        : Kenneth S. Kornman et al.

It is certified that error appears in the above-identified patent and that said Letters Patent is hereby corrected as shown below:

On the Title Page

In References Cited – Other Publications:
On Page 4, second column, Reference Cite: VARGAS-ALARCÓN, G. et al., in the parentheses in the Reference Title:
"r5"
Should read:
--rs--

In the Claims

At Column 42, Claim number 1, Line number 37:
"rs1143634; 2"
Should read:
--rs1143634;--

Signed and Sealed this
Twenty-eighth Day of January, 2020

Andrei Iancu
*Director of the United States Patent and Trademark Office*